United States Patent
Davido et al.

(10) Patent No.: US 10,034,935 B2
(45) Date of Patent: *Jul. 31, 2018

(54) NEUROATTENUATED HERPES SIMPLEX VIRUS

(71) Applicants: University of Kansas, Lawrence, KS (US); Saint Louis Univeristy, St. Louis, MO (US)

(72) Inventors: David J. Davido, Lawrence, KS (US); Lynda Anne Morrison, Webster Groves, MO (US)

(73) Assignees: University of Kansas, Lawrence, KS (US); Saint Louis University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/480,147

(22) Filed: Apr. 5, 2017

(65) Prior Publication Data

US 2017/0209565 A1    Jul. 27, 2017

Related U.S. Application Data

(63) Continuation of application No. 14/667,512, filed on Mar. 24, 2015, now Pat. No. 9,616,119.

(60) Provisional application No. 61/969,627, filed on Mar. 24, 2014.

(51) Int. Cl.
| | |
|---|---|
| *A61K 35/763* | (2015.01) |
| *A61K 39/12* | (2006.01) |
| *C12N 7/00* | (2006.01) |
| *A61K 35/76* | (2015.01) |
| *A61K 39/00* | (2006.01) |
| *C07K 14/005* | (2006.01) |
| *A61K 39/245* | (2006.01) |

(52) U.S. Cl.
CPC .................. *A61K 39/245* (2013.01)

(58) Field of Classification Search
CPC .... A61K 35/763; A61K 39/12; A61K 39/245; A61K 2039/53; A61K 35/76; C12N 7/00; C12N 2710/16632; C12N 2710/16634; C12N 2710/16643; C12N 2710/16621; C12N 2710/16651; C12N 2710/16633; C12N 2710/16661; C12N 15/8695; C12N 2710/16034; C12N 15/869; C12N 2710/16611; C07K 14/005; C07K 14/035
See application file for complete search history.

(56) References Cited

U.S. PATENT DOCUMENTS

| | | |
|---|---|---|
| 9,616,119 B2 | 4/2017 | Davido et al. |
| 2004/0228876 A1 | 11/2004 | Nishiyama |
| 2008/0069837 A1 | 3/2008 | Nishiyama |
| 2009/0317456 A1 | 12/2009 | Karrasch et al. |
| 2012/0027789 A1 | 2/2012 | Corey et al. |
| 2013/0224236 A1 | 8/2013 | Koelle et al. |
| 2014/0086947 A1 | 3/2014 | Dubensky, Jr. et al. |
| 2014/0127247 A1 | 5/2014 | Dubensky, Jr. et al. |

OTHER PUBLICATIONS

Kanai R, Zaupa C, Sgubin D, Antoszczyk SJ, Martuza RL, Wakimoto H, Rabkin SD. Effect of Y34.5 deletions on oncolytic herpes simplex virus activity in brain tumors. J Virol. Apr. 2012;86(8):4420-31. doi: 10.1128/JVI.00017-12. Epub Feb. 15, 2012.

Mabrouk Mostafa HH. Interplay Between Viral and Cellular Factors Determines the Fate of Herpes Simplex Virus type I Infection. Doctoral Dissertation, presented Mar. 25, 2014. University of Kansas, http://hdl.handle.net/1808/14534.

Mineta, Toshihiro, et al., Attenuated multi-mutated herpese simplex virus-1 for the treatment of malignant gliomas; Nature Medicine, vol. 1, No. 9, Sep. 1995, pp. 938-943.

U.S. Appl. No. 14/667,512, dated Apr. 14, 2016, Office Action.
U.S. Appl. No. 14/667,512, dated Dec. 6, 2016, Notice of Allowance.

*Primary Examiner* — Rachel B Gill
(74) *Attorney, Agent, or Firm* — Ray Quinney & Nebeker, P.C.; Paul N. Taylor

(57) ABSTRACT

A mutant HSV-1 (referred to herein as KOS-NA) was generated. KOS-NA contains novel mutations in the UL39 gene, which encodes for a protein that is a large subunit of ribonucleotide reductase (i.e., ICP6). These UL39 mutations were found to alter two amino acids in ICP6 (R950H and L393P) and are responsible for attenuation of KOS-NA in vivo, and resulted in diminished ICP6 protein levels. These novel UL39 mutations regulate the expression and/or stability of ICP6 and severely impact HSV-1 pathogenesis. Mutant HSV viruses containing these mutations appear to protect against HSV infection and can serve as therapeutic vaccines to help combat preexisting HSV infection in infected individuals.

20 Claims, 17 Drawing Sheets

L393P

```
              cldvppvlpnaymp  (SEQ ID NO:7)
UL39 KOS      ..............  
UL39 McKrae   ..............  
UL39 HG52 - old  .......l.p...t  (SEQ ID NO:8)
UL39 HG52 - new  .......l.p...t  (SEQ ID NO:9)
UL39 clin-1   .......l.p...t  (SEQ ID NO:10)
UL39 clin-2   .......l.p...t  (SEQ ID NO:11)
                              (SEQ ID NO:12)
```

```
              ewemlrqsmmkh  (SEQ ID NO:13)
UL39 KOS      ............  
UL39 McKrae   ............  (SEQ ID NO:14)
UL39 HG52 - old  ............  (SEQ ID NO:15)
UL39 HG52 - new  ............  (SEQ ID NO:16)
UL39 clin-1   ............  (SEQ ID NO:17)
UL39 clin-2   ............  (SEQ ID NO:18)
```

Figure 1B

| | | 393 → | |
|---|---|---|---|
| KOS | EMQRLCLDVPPVLPNAYMPY | (SEQ ID NO:19) |
| Syn17+ | EMQRLCLDVPPVPPNAYMPY | (SEQ ID NO:20) |
| McKrae | EMQRLCLDVPPVPPNAYMPY | (SEQ ID NO:21) |
| HG52 | EMQRLCLDVPPVPPNAYMPY | (SEQ ID NO:22) |
| KOS-NA | EMQRLCLDVPPVPPNAYMPY | (SEQ ID NO:23) |

Figure 7A

| | | 950 → | |
|---|---|---|---|
| KOS | RYEGEWEMLRQSMMKHGLRN | (SEQ ID NO:24) |
| Syn17+ | RYEGEWEMLRQSMMKHGLRN | (SEQ ID NO:25) |
| McKrae | RYEGEWEMLRQSMMKHGLRN | (SEQ ID NO:26) |
| HG52 | RYEGEWEMLRQSMMKHGLRN | (SEQ ID NO:27) |
| KOS-NA | RYEGEWEMLHQSMMKHGLRN | (SEQ ID NO:28) |

Figure 7B

```
                        SEQUENCE LISTING

<160> NUMBER OF SEQ ID NOS: 28

<210> SEQ ID NO 1
<211> LENGTH: 20
<212> TYPE: DNA
<213> ORGANISM: Artificial
<220> FEATURE:
<223> OTHER INFORMATION: WT (L393) primer

<400> SEQUENCE: 1
ctggacgttc ctccggtact                                                  20

<210> SEQ ID NO 2
<211> LENGTH: 20
<212> TYPE: DNA
<213> ORGANISM: Artificial
<220> FEATURE:
<223> OTHER INFORMATION: P393 mutant primer

<400> SEQUENCE: 2
ctggacgttc ctccggtacc                                                  20

<210> SEQ ID NO 3
<211> LENGTH: 21
<212> TYPE: DNA
<213> ORGANISM: Artificial
<220> FEATURE:
<223> OTHER INFORMATION: common downstream primer for WT (L393) primer
      and P393 mutant primer

<400> SEQUENCE: 3
tggaagacgg actccatgta g                                                21

<210> SEQ ID NO 4
<211> LENGTH: 21
<212> TYPE: DNA
<213> ORGANISM: Artificial
<220> FEATURE:
<223> OTHER INFORMATION: WT (R950) primer

<400> SEQUENCE: 4
cgtgtttcat catgctctag c                                                21

<210> SEQ ID NO 5
<211> LENGTH: 21
<212> TYPE: DNA
```

```
<213> ORGANISM: Artificial
<220> FEATURE:
<223> OTHER INFORMATION: H950 mutant primer

<400> SEQUENCE: 5
cgtgtttcat catgctctag t                                              21

<210> SEQ ID NO 6
<211> LENGTH: 22
<212> TYPE: DNA
<213> ORGANISM: Artificial
<220> FEATURE:
<223> OTHER INFORMATION: common downstream primer for WT (R950) primer
      and H950 mutant primer

<400> SEQUENCE: 6
tgcacacggc ctgcctgaag ct                                             22

<210> SEQ ID NO 7
<211> LENGTH: 14
<212> TYPE: PRT
<213> ORGANISM: Herpes Simplex Virus
<220> FEATURE:
<221> NAME/KEY: MISC_FEATURE
<223> OTHER INFORMATION: KOS UL39 (partial)

<400> SEQUENCE: 7

Cys Leu Asp Val Pro Pro Val Leu Pro Asn Ala Tyr Met Pro
1               5                   10

<210> SEQ ID NO 8
<211> LENGTH: 14
<212> TYPE: PRT
<213> ORGANISM: Herpes Simplex Virus
<220> FEATURE:
<221> NAME/KEY: MISC_FEATURE
<223> OTHER INFORMATION: KOS UL39 (partial)

<400> SEQUENCE: 8

Cys Leu Asp Val Pro Pro Val Pro Pro Asn Ala Tyr Met Pro
1               5                   10

<210> SEQ ID NO 9
<211> LENGTH: 14
<212> TYPE: PRT
<213> ORGANISM: Herpes Simplex Virus
<220> FEATURE:
<221> NAME/KEY: MISC_FEATURE
<223> OTHER INFORMATION: HG52 - old UL39 (partial)

<400> SEQUENCE: 9

Cys Leu Asp Leu Pro Pro Val Pro Pro Asn Ala Tyr Thr Pro
1               5                   10

<210> SEQ ID NO 10
<211> LENGTH: 14
<212> TYPE: PRT
<213> ORGANISM: Herpes Simplex Virus
<220> FEATURE:
<221> NAME/KEY: MISC_FEATURE
<223> OTHER INFORMATION: HG52 - new UL39 (partial)

<400> SEQUENCE: 10

Cys Leu Asp Leu Pro Pro Val Pro Pro Asn Ala Tyr Thr Pro
1               5                   10

<210> SEQ ID NO 11
```

```
<211> LENGTH: 14
<212> TYPE: PRT
<213> ORGANISM: Herpes Simplex Virus
<220> FEATURE:
<221> NAME/KEY: MISC_FEATURE
<223> OTHER INFORMATION: clinical isolate-1 (clin-1) UL39 (partial)

<400> SEQUENCE: 11

Cys Leu Asp Leu Pro Pro Val Pro Pro Asn Ala Tyr Thr Pro
1               5                   10

<210> SEQ ID NO 12
<211> LENGTH: 14
<212> TYPE: PRT
<213> ORGANISM: Herpes Simplex Virus
<220> FEATURE:
<221> NAME/KEY: MISC_FEATURE
<223> OTHER INFORMATION: clinical isolate-2 (clin-2) UL39 (partial)

<400> SEQUENCE: 12

Cys Leu Asp Leu Pro Pro Val Pro Pro Asn Ala Tyr Thr Pro
1               5                   10

<210> SEQ ID NO 13
<211> LENGTH: 12
<212> TYPE: PRT
<213> ORGANISM: Herpes Simplex Virus
<220> FEATURE:
<221> NAME/KEY: MISC_FEATURE
<223> OTHER INFORMATION: KOS UL39 (partial)

<400> SEQUENCE: 13

Glu Trp Glu Met Leu Arg Gln Ser Met Met Lys His
1               5                   10

<210> SEQ ID NO 14
<211> LENGTH: 12
<212> TYPE: PRT
<213> ORGANISM: Herpes Simplex Virus
<220> FEATURE:
<221> NAME/KEY: MISC_FEATURE
<223> OTHER INFORMATION: McKrae UL39 (partial)

<400> SEQUENCE: 14

Glu Trp Glu Met Leu Arg Gln Ser Met Met Lys His
1               5                   10

<210> SEQ ID NO 15
<211> LENGTH: 12
<212> TYPE: PRT
<213> ORGANISM: Herpes Simplex Virus
<220> FEATURE:
<221> NAME/KEY: MISC_FEATURE
<223> OTHER INFORMATION: HG52 - old UL39 (partial)

<400> SEQUENCE: 15

Glu Trp Glu Met Leu Arg Gln Ser Met Met Lys His
1               5                   10

<210> SEQ ID NO 16
<211> LENGTH: 12
<212> TYPE: PRT
<213> ORGANISM: Herpes Simplex Virus
<220> FEATURE:
<221> NAME/KEY: MISC_FEATURE
<223> OTHER INFORMATION: HG52 - new UL39 (partial)

<400> SEQUENCE: 16
```

```
Glu Trp Glu Met Leu Arg Gln Ser Met Met Lys His
1               5                   10
```

<210> SEQ ID NO 17
<211> LENGTH: 12
<212> TYPE: PRT
<213> ORGANISM: Herpes Simplex Virus
<220> FEATURE:
<221> NAME/KEY: MISC_FEATURE
<223> OTHER INFORMATION: clin-1 UL39 (partial)

<400> SEQUENCE: 17

```
Glu Trp Glu Met Leu Arg Gln Ser Met Met Lys His
1               5                   10
```

<210> SEQ ID NO 18
<211> LENGTH: 12
<212> TYPE: PRT
<213> ORGANISM: Herpes Simplex Virus
<220> FEATURE:
<221> NAME/KEY: MISC_FEATURE
<223> OTHER INFORMATION: clin-2 UL39 (partial)

<400> SEQUENCE: 18

```
Glu Trp Glu Met Leu Arg Gln Ser Met Met Lys His
1               5                   10
```

<210> SEQ ID NO 19
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: KOS UL39 (partial)

<400> SEQUENCE: 19

```
Glu Met Gln Arg Leu Cys Leu Asp Val Pro Pro Val Leu Pro Asn Ala
1               5                   10                  15

Tyr Met Pro Tyr
            20
```

<210> SEQ ID NO 20
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: Syn17+ UL39 (partial)

<400> SEQUENCE: 20

```
Glu Met Gln Arg Leu Cys Leu Asp Val Pro Pro Val Pro Pro Asn Ala
1               5                   10                  15

Tyr Met Pro Tyr
            20
```

<210> SEQ ID NO 21
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: McKrae UL39 (partial)

<400> SEQUENCE: 21

```
Glu Met Gln Arg Leu Cys Leu Asp Val Pro Pro Val Pro Pro Asn Ala
1               5                   10                  15
```

Tyr Met Pro Tyr
        20

<210> SEQ ID NO 22
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: HG52 UL39 (partial)

<400> SEQUENCE: 22

Glu Met Gln Arg Leu Cys Leu Asp Val Pro Pro Val Pro Pro Asn Ala
1               5                   10                  15

Tyr Met Pro Tyr
        20

<210> SEQ ID NO 23
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: KOS-NA UL39 (partial)

<400> SEQUENCE: 23

Glu Met Gln Arg Leu Cys Leu Asp Val Pro Pro Val Pro Pro Asn Ala
1               5                   10                  15

Tyr Met Pro Tyr
        20

<210> SEQ ID NO 24
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: KOS UL39 (partial)

<400> SEQUENCE: 24

Arg Tyr Glu Gly Glu Trp Glu Met Leu Arg Gln Ser Met Met Lys His
1               5                   10                  15

Gly Leu Arg Asn
        20

<210> SEQ ID NO 25
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: Syn17+ UL39 (partial)

<400> SEQUENCE: 25

Arg Tyr Glu Gly Glu Trp Glu Met Leu Arg Gln Ser Met Met Lys His
1               5                   10                  15

Gly Leu Arg Asn
        20

<210> SEQ ID NO 26
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: McKrae UL39 (partial)

```
<400> SEQUENCE: 26

Arg Tyr Glu Gly Glu Trp Glu Met Leu Arg Gln Ser Met Met Lys His
1               5                   10                  15

Gly Leu Arg Asn
            20

<210> SEQ ID NO 27
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: HG52 UL39 (partial)

<400> SEQUENCE: 27

Arg Tyr Glu Gly Glu Trp Glu Met Leu Arg Gln Ser Met Met Lys His
1               5                   10                  15

Gly Leu Arg Asn
            20

<210> SEQ ID NO 28
<211> LENGTH: 20
<212> TYPE: PRT
<213> ORGANISM: Herpes Simplex Virus
<220> FEATURE:
<221> NAME/KEY: MISC_FEATURE
<223> OTHER INFORMATION: KOS-NA UL39 (partial)

<400> SEQUENCE: 28

Arg Tyr Glu Gly Glu Trp Glu Met Leu His Gln Ser Met Met Lys His
1               5                   10                  15

Gly Leu Arg Asn
            20
```

NEUROATTENUATED HERPES SIMPLEX VIRUS

CROSS-REFERENCE TO RELATED APPLICATIONS

This application is a continuation of U.S. application Ser. No. 14/667,512, filed 24 Mar. 2015, which claims the benefit of and priority to U.S. Prov. App. Ser. No. 61/969,627, filed 24 Mar. 2014, the disclosures of which are incorporated in their entireties herein by reference.

GOVERNMENT FUNDING

This invention was made with government support under Grant Number R21EY019739 awarded by the National Institute of Health. The government has certain rights in the invention.

BACKGROUND

Herpes simplex virus 1 and 2 (HSV-1 and HSV-2) are two species of the herpesvirus family, herpesviridae, which cause infections in humans. Human herpesvirus infections cause a variety of illnesses including cold sores, chickenpox or varicella, shingles or herpes zoster (VZV), cytomegalovirus (CMV), mononucleosis (EBV) and various cancers, and can cause brain inflammation (encephalitis). All viruses in the herpes family produce life-long infections. HSV-1 and HSV-2 are also called Human Herpesvirus 1 and 2 (HHV-1 and HHV-2) and belong to the sub-family of neurotropic herpesviruses, which are conventionally referred to as the alpha-herpesviruses. Like all alpha-herpesviruses, HSV-1 and HSV-2 present two stages of infection: active infection and latent infection. In the active infection stage, the infected individual is symptomatic for HSV infection. In the latent infection stage, the virus becomes dormant in the nervous system of their host, which accounts for the ability of the virus to persist. An infected individual can experience multiple cycles of active and latent infection.

HSV-1 is commonly associated with recurrent herpes outbreaks of the face known as cold sores or fever blisters, whereas HSV-2 is more often associated with recurrent genital herpes.

An infection by a herpes simplex virus (HSV) is marked by watery blisters in the skin or mucous membranes of the mouth, lips, genitals or anus and buttocks. Lesions heal with a scab characteristic of herpetic disease. However, the infection is persistent and symptoms may recur periodically as outbreaks of sores near the site of original infection. After the initial, or primary, infection, HSV becomes latent in the cell bodies of nerves in the area. Some infected people experience sporadic episodes of viral reactivation, followed by transportation of the virus via the nerve's axon to the skin or mucosa, where virus replication and shedding occurs. Herpes is contagious if the carrier is producing and shedding the virus. This is especially likely during a symptomatic outbreak, but possible at other times. There is no cure yet, but there are treatments which reduce the likelihood of viral shedding.

HSV-1 is a common and significant human pathogen which causes a variety of diseases, ranging from cold sores to potentially blinding ocular infections and life-threatening encephalitis. HSV-1 establishes lifelong latent infections in neuronal cells, which reactivate periodically. Latent infection is defined as a lack of production of infectious virus at the site. Productive infection can be characterized by the expression of nearly all (about 100) viral genes in epithelial cells and fibroblasts at the periphery and the sensory neurons that innervate the site of infection.

SUMMARY

Herpes simplex viruses are major ubiquitous human pathogens. For instance, HSV-1 infects ~80% of the human population and can be life threatening if it infects neonates or immunocompromised individuals. Effective therapies in treating recurrent HSV infections are limited. In the present disclosure, a mutant HSV-1 (referred to herein as KOS-NA) was generated. KOS-NA contains novel mutations in the UL39 gene, which encodes a protein that is the large subunit of ribonucleotide reductase (i.e., ICP6). Experiments have demonstrated that presence of these UL39 mutations, which were found to alter two amino acids in ICP6, resulted in attenuation of KOS-NA in vivo and diminished ICP6 protein levels. These novel UL39 mutations were also demonstrated to regulate the expression and/or stability of ICP6 and severely impact HSV-1 pathogenesis. Mutant HSV viruses containing these mutations protect against HSV-induced disease and can serve as therapeutic vaccines to help combat preexisting HSV infection in infected individuals.

In an embodiment, a mutant herpesvirus is described. The mutant herpesvirus includes an HSV genome having a mutated UL39/ICP6 gene inserted therein. In one embodiment, the mutated UL39 gene may include one or more point mutations or in-frame deletions such as an R950H point mutation or combined R950H and L393P point mutations in ICP6. In one embodiment, the one or more point mutations or in-frame deletions render the mutant herpes virus impaired for replication and defective in establishing a latent infection. For instance, the mutant herpes virus may be incapable of causing herpes disease while still being able to replicate, to at least a limited degree, in non-neural tissue (e.g., ocular tissue) while also being essentially incapable of replicating in neural tissue. Such a virus is particularly valuable because it is able to produce a strong, long-lasting immune response due to the fact that it can replicate at least to a limited degree in non-neural tissue, while being simultaneously unable to produce symptoms of HSV infection or latent (i.e., neural) infection.

In one embodiment, the mutant herpesvirus may further include one or more additional in-frame deletions or mutations in genes other than UL39. For instance, genes such as, but not limited to, UL41, UL13, γ34.5, US3, US9, US11, and UL53 may be deleted or rendered non-functional or not transcribed by mutation. Such secondary mutations increase the safety of the mutant herpes virus and decrease the likelihood that that the point mutations in UL39 could be "rescued" by, for example, recombination with a wild-type virus.

In another embodiment, an immunogenic composition is described. The immunogenic composition may include a pharmaceutically acceptable carrier and a mutant herpesvirus that includes an HSV genome having a mutated UL39/ICP6 gene inserted therein. The mutant herpesvirus is substantially avirulent and immunogenic.

In another embodiment, a method for preventing HSV disease is described. The method may include inoculating a subject with at least a first dose of an immunogenic composition that includes a mutant herpesvirus that includes an HSV genome having a mutated UL39/ICP6 gene inserted therein. Inoculation with the immunogenic composition stimulates an immune response that protects against HSV disease. In one embodiment, the method may further include reinoculating the subject with at least a second dose of the immunogenic composition.

In yet another embodiment, a method of treating HSV disease is described. The method may include inoculating a subject having a pre-existing HSV infection with at least a first dose of a pharmaceutical composition that includes a mutant herpesvirus that includes an HSV genome having a mutated UL39/ICP6 gene inserted therein. In subjects having active or latent disease, dosing with the pharmaceutical composition stimulates an immune response that can protect against reactivation of latent HSV disease or advancement of an active HSV disease. In one embodiment, the method may further include dosing the subject with at least a second dose of the pharmaceutical composition.

In yet another embodiment, a method of making a mutant herpesvirus is described. The method includes inserting a mutated UL39/ICP6 gene that includes one or more point mutations or in-frame deletions into wild-type HSV-1 or HSV-2 background (e.g., by recombination) to produce a mutant HSV genome, packaging the mutant HSV genome in a virion, and propagating the mutant herpesvirus.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 1A and 1B illustrates sequence alignments of ICP6 from KOS-NA and different HSV strains in the regions of L393 and R950.

FIGS. 7A and 7B are sequence alignments of two regions in ICP6 from KOS-NA and different HSV strains.

DETAILED DESCRIPTION

Figures 2A, 2B:
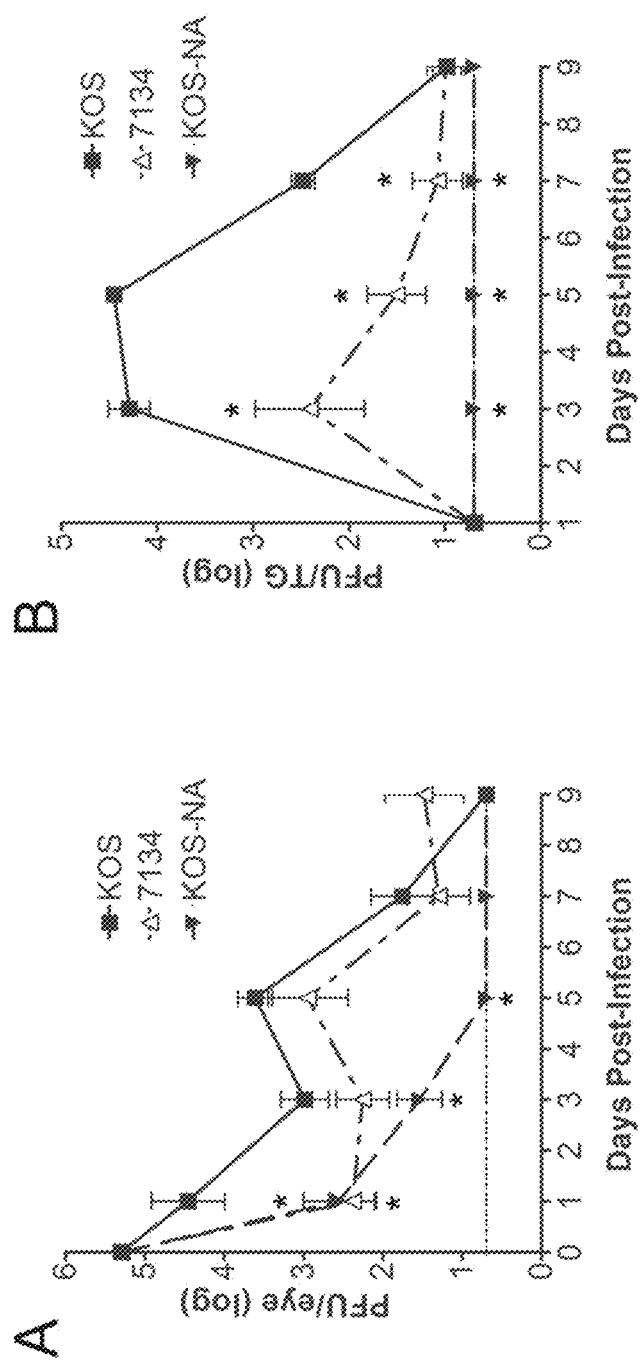
FIGS. 2A and 2B illustrate data relating to acute replication of KOS-NA. A) Acute ocular replication of KOS-NA in the mouse. Mice were infected with $2 \times 10^5$ plaque forming units per eye, and tear film was collected from each eye on days 1, 3, 5, 7, and 9. The amount of infectious virus collected in each sample was determined by plaque assay. B) Acute replication of KOS-NA in mouse trigeminal ganglia (TG). Mice were infected as described above, and TG were collected on the indicated days. TG were then homogenized, and the amount of infectious virus present was determined by plaque assay. In both A and B, results shown are logarithmic means (n=6 sample per group per time point), with the error bars indicating the SEM. The horizontal dotted lines represent the lower limit of detection. * t test, p<0.05.

Herpes simplex viruses are major ubiquitous human pathogens. For instance, HSV-1 infects ~80% of the human population and can be life threatening if it infects neonates or immunocompromised individuals. Effective therapies in treating recurrent HSV infections are limited. In the present disclosure, a mutant HSV-1 (referred to herein as KOS-NA) was generated. KOS-NA contains novel mutations in the UL39 gene, which encodes a protein that is the large subunit of ribonucleotide reductase (i.e., ICP6). Experiments have demonstrated that presence of these UL39 mutations, which were found to alter two amino acids in ICP6, resulted in attenuation of KOS-NA in vivo and diminished ICP6 protein levels. These novel UL39 mutations were also demonstrated to regulate the expression and/or stability of ICP6 and severely impact HSV-1 pathogenesis. Mutant HSV viruses containing these mutations protect against HSV-induced disease and can serve as therapeutic vaccines to help combat preexisting HSV infection in infected individuals.

It has now been found that mutations in conserved regions of UL39, which encodes the protein ICP6 of HSV, can alter the ability of HSV-1 to cause HSV induced disease. Based on sequence alignments and conservation patterns, it is hypothesized that analogous mutations in conserved regions of UL39 occurring in the gene encoding ICP6 for both the HSV-1 and HSV-2 may result in an avirulent mutant virus. The mutations within conserved regions may alter protein stability or, because ICP6 functions as part of a protein complex, mutations within conserved regions of UL39 may alter the ability of ICP6 to functionally interact with its binding partners, affecting both their biochemical and biological functions. Likewise, it has been found that UL39 mutants are able to protect against HSV disease. Viruses having mutations in UL39 have only limited ability to replicate in non-neuronal tissue, essentially no ability to replicate in neural tissue, essentially no ability to cause latent infection, and no ability to reactivate from latency.

Referring now to FIGS. 1A and 1B, sequence alignments showing conserved regions in the vicinity of L393 and R950 are illustrated. In the alignments, ICP6 protein sequence of the KOS isolate is shown on top line. Conserved residues in the aligned sequences are indicated by dots below the KOS sequence; changes are indicates by showing the changed amino acid(s) below the KOS sequence.

The amino acid sequence alignments shown in FIGS. 1A and 1B indicate that L393 is not well conserved between strain KOS and other HSV strains; syn17+ (HSV-1), McKrae (HSV-1) and HG52 (HSV-2) and two new clinical isolates (din 1 and din 2), which, like KOS-NA, encode a proline at the L393 site. On the other hand, R950 is conserved between all HSV-1 and HSV-2 strains we examined (i.e., KOS, syn17+, McKrae, HG52, din 1, and din 2), suggesting that the R950H mutation in KOS-NA is unique. Arginine to histidine is generally classified a conservative mutation due to the fact that both amino acids have relatively bulky, basic side chains. The fact that R950 is so well-conserved and that virus having the R950H mutation has such a pronounced phenotype is surprising and unexpected and indicates that R950 may be particularly crucial to the structure and/or function of ICP6. And while the L393P mutation may not alone be responsible for the observed phenotype of KOS-NA, it may act synergistically with the observed R950H mutation to produce the phenotype of KOS-NA. In addition, L393 and R950 are within regions of high sequence conservation, which is particularly true in the case of R950. In general, the ICP6 protein is well conserved, particularly in the C-terminal two thirds of the protein. Because the conserved regions extend beyond L393 and R950, they can provide greater flexibility in designing a mutant HSV that is avirulent.

Additionally, regions that are conserved in the ICP6 protein between HSV-1 and HSV-2 may also be conserved in about 20 other α-herpesviruses, and thereby mutations to the conserved regions of the α-herpesviruses may also produce avirulent α-herpesviruses. Examples of some of these α-herpesviruses can include bovine herpesviruses 1 or 5 (BHV-1 or BHV-5), equid herpesviruses 1, 4, or 9 (EHV-1, EHV-4, or EHV-9), suid herpesvirus 1 or pseudorabiesvirus (PRV), varicella zoster virus (VZV), canid herpesvirus 1 (CHV-1), felid herpesvirus 1 (FHV-1), macropodid herpesvirus 1 (MHV-1), cercopithecine herpesviruses 2 or 9 (CpHV-2 or CpHV-9), macacine herpesvirus 1 which is commonly known as the herpes B virus, or papiine herpesvirus 2 (PHV-2). This is not an exhaustive list of all herpesviruses that encode an ICP6-like protein, but rather is meant to illustrate that herpesviruses exist throughout the animal kingdom. Based on the sequence alignments and results illustrated herein, it is reasonable to conclude that such viruses may rely on an ICP6-like protein for their ability to replicate efficiently and cause disease in their animal hosts.

Mutant Herpes Viruses

In one embodiment, a mutant herpesvirus is described. The mutant herpesvirus includes an HSV genome having a mutated UL39/ICP6 gene inserted therein. Suitable examples of mutations may include, but are not limited to, point mutations or in-frame deletions in UL39 that alter the structure or amino acid sequence of ICP6. Suitable point mutations or in-frame deletions may be placed in the UL39 sequence in the vicinity of the well-conserved regions of the amino acid sequence of ICP6 around L393 or R950. In a specific embodiment, the mutated UL39 gene may include an R950H point mutation in ICP6 or combined R950H and L393P point mutations in ICP6.

In one embodiment, the one or more point mutations or in-frame deletions render the mutant herpes virus impaired for replication and defective in establishing a latent infection. Such a mutant virus may be termed "avirulent." As used herein, the term "avirulent" is meant to refer to a mutant virus that is unable to cause disease or significantly inhibited from causing disease. For example, an "avirulent" virus can be considered to be replication-impaired, repression-prone, and/or interferon-sensitive. For instance, the mutant herpes virus may be incapable of causing herpes disease while still being able to replicate, to at least a limited degree, in non-neural tissue (e.g., ocular tissue) while also being essentially incapable of replicating in neural tissue.

Such a virus is particularly valuable because it is immunogenic and able to produce a strong, long-lasting immune response due to the fact that it can replicate at least to a limited degree in non-neural tissue, while being simultaneously unable to produce symptoms of HSV infection or latent (i.e., neural) infection. As used herein, the term "immunogenic" is meant to refer to a mutant virus that is capable of causing or producing an immune response. For example, an "immunogenic" virus may be useful in an immunogenic composition, such as a vaccine.

The mutant herpesviruses disclosed herein may be characterized by one or more of the following: being incapable of causing a herpes disease; being able to replicate, to at least a limited degree, in non-neural tissue; being essentially incapable of replicating in neural tissue; being incapable of initiating latent HSV infection; or being able to produce a long-lasting immune response while being incapable of causing a herpes disease.

In one embodiment, the mutant herpesvirus may further include one or more additional in-frame deletions or mutations in genes other than UL39. For instance, genes such as, but not limited to, UL41, UL13, γ34.5, US3, US9, US11, and UL53 may be deleted or rendered non-functional or not transcribed by mutation. For instance, the protein gene product of one or more of the foregoing genes could be eliminated by deletion of the open reading frame, or mutation of the N-terminus of the gene by insertion of a stop codon. Either way, the result is no expression of the viral protein product. Such secondary mutations increase the safety of the mutant herpes virus and decrease the likelihood that that the point mutations or in-frame deletions in UL39 could be "rescued" by, for example, recombination with a wild-type virus.

In one embodiment the mutant herpesvirus may be one of a herpes simplex virus 1 (HSV-1) or herpes simplex virus 2 (HSV-2). As is illustrated in FIGS. 1A and 1B, the amino acid sequence of ICP6 is well-conserved across HSV strains. In one embodiment, the mutant herpesvirus may be generated from an HSV-1 virus with a mutated UL39 gene. In another embodiment, the mutant herpesvirus may be generated from an HSV-2 virus with a mutated UL39 gene. Thus, in one embodiment, the mutant herpesvirus may be an HSV-1 virus with an HSV-1 genome having a mutated HSV-1 UL39/ICP6 gene inserted therein. Likewise, the mutant herpesvirus may be an HSV-2 virus with an HSV-2 genome having a mutated HSV-2 UL39/ICP6 gene inserted therein. In other embodiments, a mutated HSV-1 UL39/ICP6 gene may be inserted in an HSV-2 genomic background, or a mutated HSV-2 UL39/ICP6 gene may be inserted in an HSV-1 genomic background.

Immunogenic Compositions

In accordance with the discussions of mutant HSV-1 and/or mutant HSV-2, either the mutant HSV-1 and/or mutant HSV-2 as well as any mutant alpha-herpesvirus can be used in an immunogenic composition such as a vaccine. Methods of preparing vaccines to include a mutant virus are well established in the art of vaccines. References to HSV should be considered to also refer to any of the alpha-herpesviruses that encode a mutated ICP6-like protein.

In one embodiment, the mutant HSV can be used in a vaccine or other composition to inhibit wild-type HSV replication, and thereby inhibit or prevent the diseases caused by HSV infections. Data for the mutant HSV viruses encoding for mutant ICP6 indicate that alterations of ICP6 at or in the region of R950 (e.g., R950H), or at or in the region of R950 and L393 inhibits HSV replication and ability to cause HSV disease and latent infection in comparison with wild-type HSV-1, while still being immunogenic. Also, the mutant HSV-1 encoding mutant ICP6 was shown to exhibit a reduced capacity to replicate in neurons.

In one embodiment, the mutant HSV encoding the mutant ICP6 protein can be introduced into an individual that has been infected or may become infected with a HSV virus. Thus, the mutant HSV can treat, limit, and/or prevent wild-type HSV infections as well as disease states caused by wild-type HSV. For example, mutant HSV-1 viruses can be used to prevent wild-type HSV-1 infections and mutant HSV-2 viruses can be used to prevent wild-type HSV-2 infections. In addition, there is evidence to suggest that HSV vaccines can cross-protect among strains. For instance, it is likely that an HSV-1 vaccince can protect against HSV-2, and vice versa. Likewise, any mutant alpha-herpesvirus that encodes a mutant ICP6 protein can be used to prevent infection of animals with its corresponding wild-type alpha-herpesvirus.

A vaccine can be prepared which includes mutant HSV-1 and/or mutant HSV-2 with one or more excipients and/or adjuvants. In one embodiment, an immunogenic composition may include a pharmaceutically acceptable carrier and a mutant herpesvirus that includes an HSV genome having a mutated UL39/ICP6 gene inserted therein. As discussed above, the mutations in the mutated genome may include, but are not limited to an R950H point mutation in ICP6 or R950H and L393P point mutations in ICP6. In any case, the mutant herpesvirus is substantially avirulent and immunogenic. In another embodiment, the mutant HSV viral genome encoding for mutant ICP6 may be included in a vaccine. The vaccine can contain genetic material, such as a heterologous gene insert expressing the mutant protein. In such a case, the mutant ICP6 can be expressed in cells of a susceptible species immunized with the vaccine containing mutant HSV-1 and/or mutant HSV-2. Immunity against wild type HSV-1 and/or HSV-2 can thereby be conferred in a species and/or tissue normally susceptible to HSV-1 and/or HSV-2 infection. Also, a vaccine that contains a mutant HSV-1 and/or mutant HSV-2 may be taken by subjects who are already infected by HSV-1 and/or HSV-2 to impair or inhibit its replication and thereby impair or prevent recurrent outbreaks of herpes disease.

The vaccine can be a pharmaceutical preparation as is standard in the art. The vaccine can be administrable subcutaneously, intra-muscularly, intra-dermally, epithelially, nasally, vaginally, or orally and can comprise excipient(s) suitable for the selected administration route. The pharmaceutical preparation can be capable of protecting a patient immunized therewith against infection or the consequences of infection by a corresponding wild-type virus.

Also, the present invention can include an assembly comprising a pharmaceutical for prophylaxis or for therapy as described herein in a container. The container can contain the mutant HSV-1 and/or mutant HSV-2. The container can be a pre-filled syringe or glass vial/ampoule with printed instructions on or accompanying the container concerning the administration of the pharmaceutical to a patient to prevent or treat conditions caused by infection with wild-type HSV-1 and/or HSV-2.

A vaccine or other pharmaceutical preparation containing the mutant HSV-1 and/or mutant HSV-2 as described can be prepared in accordance with methods well known in the art wherein the mutant HSV is combined in admixture with a suitable vehicle. Suitable vehicles include, for example, saline solutions, or other additives recognized in the art for use in compositions applied to prevent viral infections. Such vaccines will contain an effective amount of the mutant HSV as hereby provided and a suitable amount of vehicle in order to prepare a vaccine useful for effective administration to the host.

Dosage rates of the vaccine can be determined according to known methods. For example, dosage rate may be determined by measuring the optimum amount of antibodies directed against a mutant HSV resulting from administration of varying amounts of the mutant HSV in vaccine preparations. Suitable vehicles and their formulation are described in 'Remington's Pharmaceutical Sciences' (Mack Publishing Co, Easton, Pa., ed. A R Gennaro), by E W Martin, and by F Rola, which is incorporated herein by specific reference. Such compositions contain an effective amount of the mutant HSV-1 and/or mutant HSV-2 with a suitable amount of carrier vehicle in order to prepare therapeutically acceptable compositions suitable for effective administration to the host.

Vaccines can be prepared with excipients which are pharmaceutically acceptable and compatible with the active ingredient. Suitable excipients are, for example, water, saline, dextrose, glycerol, trehalose, or the like and combinations thereof. In addition, if desired, the vaccine may contain minor amounts of auxiliary substances such as other stabilizers and/or pH buffering agents, which enhance the stability and thus the effectiveness of the vaccine.

Vaccines may be configured to be administered parenterally, by injection, for example, subcutaneously or intraepithelially (with or without scarification). Additional formulations which are suitable for other modes of administration, such as oral, vaginal and nasal formulations are also provided. Oral formulations include such normally employed excipients as, for example, pharmaceutical grades of trehalose, mannitol, lactose, starch, magnesium stearate, sodium saccharine, cellulose, magnesium carbonate, and the like.

The compositions may take the form of solutions, suspensions, tablets, pills, capsules sustained release formulations or powders.

Vaccines can be administered in a manner compatible with the dosage formulation, and in such amount as will be prophylactically effective. The quantity to be administered will have been predetermined from preclinical and clinical (phase I) studies to provide the optimum immunological response.

The vaccine may be given in a single dose schedule or in a multiple dose schedule, as needed or desired. A multiple dose schedule is one in which a primary course of vaccination with 1-3 separate doses elicits an immune response, and is followed by other doses given at subsequent time intervals that maintain, reinforce, and/or boost the immune response to HSV. For example, at 1-4 months for a second dose, and if needed, a subsequent dose(s) after several months. The dosage regimen will also, have been determined from preclinical and clinical studies as maintaining the optimum immunological response over time.

The vaccine including the mutant HSV-1 and/or mutant HSV-2 may be taken by subjects during primary or secondary infections with wild-type HSV to curtail the severity and duration of symptoms. The vaccine including mutant HSV-1 and/or mutant HSV-2 may also reduce the frequency and severity of recurrent herpetic disease. Single injection of mutant HSV encoding mutant ICP6 may provide life-long protection against recurrent outbreaks of the corresponding wild-type HSV virus. However, multiple administrations may be utilized. The vaccine of the present invention can improve treatment and prevention of HSV infections and other disease states related to HSV infection. The present invention may be applied to a subject during latent infection of HSV to impair or prevent recurrent herpetic disease, as well as reduce their rate of infectious HSV shedding. Thus, the vaccine can also reduce the relative risk that an HSV carrier will transmit the infection to other persons.

Additionally, the mutant HSV-1 and/or mutant HSV-2 can also be included in vaccines, as well as methods of treatment and/or prevention, to reduce or inhibit blepharitis (eyelid disease), keratitis (corneal opacity), and latency. Methods of treating and/or preventing blepharitis (eyelid disease), keratitis (corneal opacity), and latency can include providing the mutant HSV-1 and/or mutant HSV-2 to a subject.

Methods for Preventing HSV Infection

In one embodiment, the present invention can include a method for preventing HSV infection with an immunogenic composition that can stimulate an immune response that protects against HSV disease. In one embodiment, the method includes steps of inoculating a subject with at least a first dose of the immunogenic composition that includes a mutant HSV virus having a mutated UL39/ICP6 gene inserted therein. Mutant HSV viruses that can be included in the immunogenic composition include those described herein above.

In one embodiment, the immunogenic composition can administered to the subject in a therapeutically effective amount to induce an immunological response to the mutant herpesvirus. The immunological response can be sufficient to provide immunity to a corresponding wild-type herpesvirus. It is possible that the immunity can be for life of the subject, or possibly for a limited number of years.

In the instance that immunity may not be for life of the subject, the immunization method can include administering a booster dose of an immunogenic composition that includes the immunogenic composition, wherein the mutant herpesvirus is substantially avirulent and immunogenic.

The immunogenic composition can be administered in a method for treating, inhibiting, and/or preventing a herpesvirus infection. For example, the immunogenic composition can be administered for a method of treating, inhibiting, and/or preventing genital herpes, cold sores, or any other animal disease or condition caused by an alpha-herpesvirus.

Likewise, in one embodiment, the present invention can include a method of immunizing a subject. Such a method can include administering to the subject an immunogenic composition having a mutant herpesvirus that has a mutated UL39 gene inserted therein. The mutant herpesvirus may have one or more in-frame deletions or point mutations in or around R950 and L393 of UL39. The mutation can be sufficient to impair replication of the herpesvirus. Also, the mutation can reduce clinical severity of a herpesvirus infection and/or herpesvirus-mediated diseases.

In one embodiment, the present invention can include a method of mutating a herpesvirus. Such a method can include generating one or more mutations in a conserved region of the UL39 gene, such as in the coding region encoding amino acids R950 and L393, and forming the mutant virus to have the mutated gene encoding for mutant ICP6. The gene mutation can be within the DNA coding sequence for at least one region of ICP6 that is substantially conserved between herpes simplex virus 1 (HSV-1) and herpes simplex virus 2 (HSV-2), or with other alpha-herpesviruses. The mutant herpesvirus can be substantially avirulent and immunogenic.

In one embodiment, the present invention includes a method of making a mutant herpesvirus. The method includes inserting a mutated ICP6/UL39 gene that includes one or more point mutations or in-frame deletions into wild-type HSV-1 or HSV-2 background to produce a mutant HSV genome, packaging the mutant HSV genome in a virion, and propagating the mutant herpesvirus. The mutated gene generated in the method can be recombined into the HSV-1 or HSV-2 genome after transfection into mammalian cultured cells, packaged into a virion by the culture cells, and propagated by methods known in the art.

In one embodiment, the manufactured virus can be made to include mutations and/or deletions in other regions of the genome. As discussed above, genes such as, but not limited to, UL41, UL13, γ34.5, US3, US9, US11, and UL53 may be deleted or rendered non-functional or not transcribed by mutation. For instance, the protein gene product of one or more of the foregoing genes could be eliminated by deletion of the open reading frame, or mutation of the N-terminus of the gene by insertion of a stop codon. Either way, the result is no expression of the viral protein product. Such secondary mutations increase the safety of the mutant herpes virus and decrease the likelihood that that the point mutations or in-frame deletions in UL39 could be "rescued" by, for example, recombination with a wild-type virus.

EXAMPLES

Example 1

In the process of generating HSV-1 mutants in the viral regulatory gene, infected cell protein 0 (ICP0), a viral mutant was generated an isolated, termed KOS-NA, that was severely impaired for acute replication in the eyes and trigeminal ganglia (TG) of mice, defective in establishing a latent infection, and reactivated poorly from explanted TG. To identify the secondary mutation(s) responsible for the impaired phenotypes of this mutant, the KOS-NA genome was sequenced and it was noted that it contained two nonsynonymous mutations in the UL39 gene. These mutations resulted in two amino acid (aa) changes in ICP6: Lysine (L) to Proline (P) at residue 393, and Arginine (R) to Histidine (H) at residue 950.

UL39 encodes the large subunit of ribonucleotide reductase, also known as ICP6. The ribonucleotide reductase enzyme complex is essential for viral DNA replication because it converts ribonucleotides to deoxyribonucleotides. Although this gene is not essential for viral growth and replication in dividing cell lines, it is important for viral replication in quiescent cells such as neurons, and several published studies have shown that UL39 mutants are severely impaired for viral replication, establishment of latency, and/or reactivation in murine models of HSV-1 replication. Based on that, experiments were undertaken to test whether KOS-NA's observed attenuation is related to its UL39 mutations.

To investigate this possibility, the wild-type copy of UL39 was inserted into the KOS-NA (KOS-NAR) to see if the mutant UL39 phenotype could be "rescued," and, independently, the mutated UL39 gene was introduced into the wild-type KOS background to determine if the mutant phenotype could be replicated. The acute replication of both viruses was examined in the eyes and TG of mice. Results from these experiments indicate that amino acids 393 and/or 950 of ICP6 are essential for high levels of acute replication in the eyes and TG of CD-1 mice, which facilitates the establishment of an efficient latent infection.

Materials and Methods

Cell lines and viruses. Vero cells and L7 (ICP0-containing Vero cells) were cultured in Dulbecco's modified Eagle's medium (DMEM) supplemented with 5% fetal bovine serum (FBS), 100 µg/ml penicillin, 100 units/ml streptomycin, and 2 mM L-Glutamine. The wild-type HSV-1 strain KOS, 7134 (an ICP0-null mutant virus), KOS-NA, KOS-NA marker rescue (MR), UL39 L393P/R950H, HrR3 (a virus that contains a lacZ insertion in UL39 (11), kindly provided by Dr. Sandra Weller) and HrR3 R viruses were propagated and titered as previously described (15, 16).

Antibodies. Primary antibodies used were anti-ICP0 mouse monoclonal antibody 11060 (Santa Cruz Biotechnology, cat. no. sc-53070), diluted 1:1000; β-Actin-specific, rabbit polyclonal antibody (Santa Cruz Biotechnology, cat. no. sc-1616) diluted 1:1000; ICP6 mouse monoclonal antibody, kindly provided by Drs. Howard Marsden and Roger Everett, diluted 1:1000; and anti-UL40 mouse monoclonal antibody, kindly provided by Drs. Howard Marsden and Roger Everett, diluted 1:250. Secondary antibodies used were peroxidase-conjugated goat antirabbit (Jackson Immunoresearch) diluted 1:1000, and peroxidase-conjugated goat antimouse (Jackson Immunoresearch) diluted 1:1000.

High throughput sequencing of KOS-NA genome: The secondary mutations in the KOS-NA viral genome were characterized via whole genome sequencing as previously described for the wild type strain KOS. Briefly, genomic DNA from the strain was isolated from infected Vero cells and used to construct a standard Illumina library. Following sequencing, the raw unpaired 42-bp reads were passed through the SolexaQAperlscripts to remove low quality reads and aligned against both the Rhesus macaque and human genomes using Bowtie to eliminate any reads derived from the Vero cell host. The remaining high-quality reads were de novo assembled with Velvet, and contigs>100-bp were assembled against the reference HSV-1 strain 17 syn+ genome using Seqman pro (DNASTAR, Inc.). The final KOS-NA genome is 152,011-bp, has 13 shorts gaps totaling 1,582-bp exclusively at variable number tandem repeat (VNTR) regions, and was sequenced to an average per-bp coverage of 3,104×. We transferred annotation from the reference genome strain 17 syn+ using RATT and confirmed the final KOS-NA annotation manually. To identify and characterize nucleotide differences between KOS and KOS-NA, the genomes were aligned using FSA and applied a custom R script [www_r-project_org]. 34 SNPs were identified discriminating the strains, including 17 nonsynonymous changes residing in six genes (10 of which are the introduced phosphorylation mutations in both copies of ICP0, 2 in the UL39 gene, 4 in both copies of ICP4 gene, and 1 in gI gene), and 11 short (1-4 bp) insertion-deletion events, all present outside of coding regions.

Construction of UL39 mutant and rescue viruses: KOS-NA contains mutations in ICP0 phosphorylation sites and was constructed as previously described. To generate the UL39 L393P/R950H mutant, the UL39 gene was cloned out of the KOS-NA viral genome using BglII and KpnI sites and ligated into pSP72 using the same sites (pSP72:UL39). Vero cells were plated on 60 mm dishes at $4 \times 10^5$ cells per plate. Twenty-four hr post-plating, cells were co-transfected with 1 µg of viral DNA from HrR3 and 2.5 µg pSP72:UL39 plasmid digested with BglII and KpnI. Transfections were performed using Fugene HD (Roche) at a ratio of 3:1 (µl of transfection reagent to µg of DNA) based on manufacturer recommendations. Mutants were identified by blue/white selection in the presence of X-gal. White plaques were isolated, and viral isolates containing the two mutated sites were screened with the PCR amplification refractory mutation system (ARMS) technique using the following primers: codon 393 site; WT (L393) primer (5'-CTGGACGTTC-CTCCGGTACT-3') (SEQ ID NO:1), P393 mutant primer (5'-CTGGACGTTCCTCCGGTACC-3') (SEQ ID NO:2), and common primer (5'-TGGAAGACGGACTCCATG-TAG-3') (SEQ ID NO:3); codon 950 site; WT (R950) primer (5'-CGTGTTTCATCATGCTCTAGC-3')_(SEQ ID NO:4), H950 mutant primer (5'-CGTGTTTCATCATGCTCTAGT-3') (SEQ ID NO:5), and common primer (5'-TGCACACG-GCCTGCCTGAAGCT-3') (SEQ ID NO:6). Candidates were confirmed by DNA sequencing. Correct insertion of the gene into the viral genome was confirmed by XhoI digests followed by Southern blot analysis. The KOS-NAR virus was generated by co-transfection of 1 of KOS-NA viral DNA and 2.5 µg of pKHF plasmid, which contains WT UL39, digested with EcoRI and XbaI. Plaques were picked randomly and screened with the PCR ARMS technique as described above. Confirmation of the rescue of the mutation was performed by PCR, followed by sequencing and Southern blot analyses using the restriction enzyme BamHI. The HrR3 R (rescue) virus was constructed by cotransfecting Vero cells with 1 µg of HrR3 viral DNA and 2.5 µg of pKHF plasmid digested with EcoRI and XbaI. Rescuants were identified by blue/white selection and confirmed by Southern blot analysis by digesting the viral DNA with XhoI.

Ocular infection of mice. CD-1 out-bred female mice (6-7 weeks old) were obtained from Charles Rivers Laboratories (Shrewsbury, Mass.), cared for according to Guide for the Care and Use of Laboratory Animals, and infected as previously described. Briefly, mice were anesthetized by intraperitoneal injection of ketamine (75-100 mg/kg of body weight) and xylazine (10 mg/kg of body weight). Corneas were scarified with a 26-gauge needle and were infected with KOS, 7134, KOS-NA, KOS-NAR, UL39 L393P/R950H, or HrR3 R at $2 \times 10^5$ PFU of virus per eye in 3-5 µl medium.

Determination of viral titers in eyes and TG. Four hours and 1, 3, 5, 7, and/or 9 days post-infection (post infection), eye swabs and/or TG samples were collected. For eye swabs, tear film was collected by swabbing the eye with cotton-tipped swabs and placed in microfuge tubes containing 500 µl 5% FBS growth medium. For TG samples, the mice were sacrificed by $CO_2$ asphyxiation, and the TG were removed and placed in microfuge tubes with 500 µl growth medium and 100 µl of 1 mm beads. These samples were homogenized using a Mini-Beadbeater 8 (BioSpec, Bartlesville, Okla.). In all cases, the wild-type, UL39 L393P/R950H, and HrR3 R viruses were titered on Vero cells, and KOS-NA and KOS-NAR viruses were titered on L7 cells. Statistical analyses were performed using student's t test Latent viral genome loads in TG. At 28-30 days post infection, latently infected TG were collected, and DNA was isolated from each TG as previously reported (26). PCR primers for the HSV-1 UL50 gene and the mouse adipsin gene were used to amplify viral DNA and as a loading control for cellular DNA, respectively. Real time PCR samples were performed in a total volume of 25 µl containing FastStart SYBR Green Master (Rox) (Roche, Indianapolis, Ind.) and primers [300 nM] in an ABI Prism 7500 real-time PCR system (Applied Biosystems, Foster City, Calif.). UL50 PCR samples contained 125 ng of DNA per reaction, adipsin PCR samples contained 10 ng of DNA per reaction, and all samples were analyzed in duplicate or triplicate. Standard curves for each PCR condition were carried out as described before to quantify the amount of viral DNA present in each sample relative to the adipsin gene using the 2-ΔΔct method. Statistical analyses were performed using one-way ANOVA test.

Viral explant-induced reactivation studies. Days 28-30 post infection, latently infected mice were sacrificed, each TG was collected and cut into 8 pieces and cultured on Vero cells in a well of a 24-well plate. Each well contained 1.5 ml of Vero cell medium. The cultures were sampled daily for up to 16 days for the presence of infectious virus by cytopathic effect on Vero cells for KOS and on L7 cells for KOS-NA and 7134 infected samples. At day 10 post-explantation, cultures were heat-shocked at 43° C. for 3 h as an additional stimulus for reactivation. Statistical analyses were performed using the Fisher's exact test.

Western blot. ICP6 and UL40 protein levels: $1\times10^5$ Vero cells were plated per well of a 12-well plate. Twenty four hour post-plating, cells were infected at an MOI of 2 for each virus. Samples were harvested 24 h post-infection in 50 µL 1× Laemmeli buffer (100° C.) supplemented with 1× protease inhibitors (Leupeptin Aprotinin 1 µg/mL, PMSF 1 mM). Samples were heated at 95° C. for 5 min, vortexed, centrifuged, and loaded on a 4-12% gradient gel (Invitrogen), and ran at 120V for 1 h. Proteins were transferred to nitrocellulose membranes using a semidry transfer unit (GE Health Care, cat. no. TE77). Each membrane was blocked in 5% bovine serum albumin (BSA) in TBS and 0.1% Tween-20 (TBS-T) for 1 h at room temperature. Primary antibodies were incubated with membranes overnight at 4° C., then the membranes were washed 3 times in TBS-T, and secondary antibodies were added at room temperature for 1 h. Membranes were washed 3 times in TBS-T and developed using SuperSignal West Pico chemiluminescent substrate (Thermo Fisher Scientific, cat. no. 34087). Pictures were captured with a Kodak 4000R image station.

Immunoprecipitations. Vero cells were plated in 60 mm dishes at $5\times10^5$ cells per plate. Twenty four hr later, cells were mock infected or infected with KOS at MOI of 2 or KOS-NA at MOI of 5 for 24 h. Cells were harvested in 100 µL of a buffer containing 100 mM Tris-HCl pH 8, 50 mMNaCl, 10% glycerol, 20 mM β-mercaptoethanol, and 1% Nonidet P-40 with protease inhibitors as described above. Samples were sonicated at 100 W for 30 sec, incubated on ice for 30 min, and centrifuged at 15K rpm for 10 min at 4° C. After aspirating the beads buffer, 50 µL protein G Dynabeads (Invitrogen) were incubated with 200 µL of PBS with 0.05% Tween-20 and 5 µL of an UL40 mouse monoclonal antibody (kindly provided by Dr. Everett), by rotating for 1 h at room temperature. Beads bound to the antibody were washed with PBS and 0.05% Tween-20 and incubated with the sample lysates, rocking at 4° C. overnight. The beads were then washed twice with PBS-Tween and transferred to new tubes. Fifty microliters of 1× Laemmeli buffer (100° C.) with protease inhibitors were added to each sample and samples were boiled for 5 min, vortexed, boiled again, and vortexed twice for 1 min each. Western blot analyses were performed as described in the previous section.

Results

Mutations in KOS-NA impair acute viral replication in the eyes and trigeminal ganglia (TG). Acute replication of KOS-NA at the periphery in ocular epithelia was initially examined. For these experiments, CD-1 mice were infected with $2\times10^5$ plaque forming units (PFU) of wild type HSV-1 (KOS), the ICP0 null mutant, 7134, and KOS-NA per eye. 7134 was used as an attenuated control virus in these experiments (27). Eye swabs from mice were taken at days 1, 3, 5, 7, and 9 post infection. As shown in FIG. 2A, the replication of KOS-NA on days 1 and 3 post infection was 79-fold (t test, p=0.015) and 25-fold (t test, p=0.006) lower than KOS, respectively. On day 5 post infection, no KOS-NA infectious virus was detected (≥1000-fold decrease compared to KOS, t test, $p=3.9\times10^{-5}$), which was followed by 11-fold reduction on day 7 post infection. Interestingly, the replication of KOS-NA was more impaired than the ICP0-null virus, 7134, on days 3, 5, and 7 post infection. When acute replication in neurons of the TG was examined, KOS-NA showed no detectable replication for all the time points examined. Relative to KOS titers, these represented decreases of at least 3981-, 5011-, and 63-fold on days 3, 5, and 7 post infection (t test, $p=1.4\times10^{-5}$, $3.5\times10^{-9}$, and $2.5\times10^{-5}$, respectively). 7134, as expected was capable of replicating in TG neurons of CD-1 mice, albeit poorly (FIG. 2B).

Figure 3:
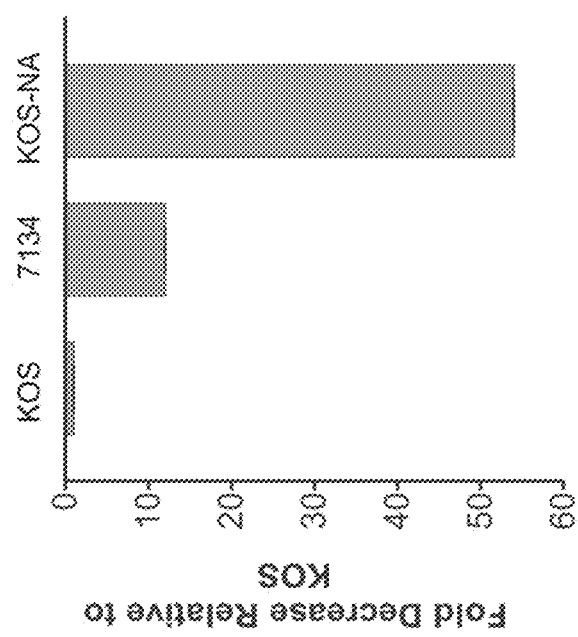
FIG. 3 illustrates viral genome loads in latent TG. Mice were infected with $2 \times 10^5$ plaque forming units per eye, and TG were collected 28-30 days post infection. DNA was extracted from latent TG, and the amount of HSV-1 DNA present was quantified by real time PCR (n=4-10 TG per group). Results shown are the fold reduction compared to KOS.

Mutations in KOS-NA reduced the establishment of latency. To quantify the relative amount of viral DNA present in latently infected neurons, TG were collected at days 28-30 post infection and assayed for the presence of HSV-1 DNA using quantitative real time PCR. As shown in FIG. 3, the amounts of latent viral DNA present in TG were significantly reduced for KOS-NA (64-fold, one way ANOVA, p<0.05) and 7134 (12-fold, one way ANOVA, p<0.05) relative to the level of KOS.

Figure 4:
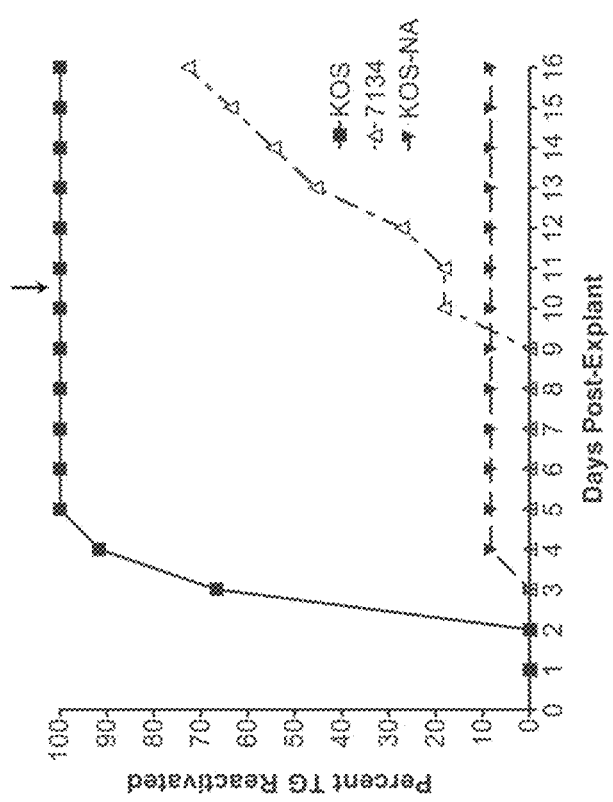
FIG. 4 illustrates explant induced reactivation of KOS-NA. Mice were infected with $2 \times 10^5$ plaque forming units per eye. On day 28-30 post infection, TG were collected and explanted onto Vero cells. The time required for each virus to reactivate from the latent TG was determined by assaying the culture medium daily for the presence of infectious virus. Each time point represents the cumulative percentage of samples that reactivated (n=19-20 TG per group). The arrow at the top of the graph indicates that after day 10, samples were heat shocked at 43° C. for 3 hours.

The efficiency of KOS-NA reactivation is reduced. To determine if the efficiency and kinetics of reactivation from latency were altered for KOS-NA, latent TG of all viral groups were collected on days 28-30 post infection and subsequently cultured by explantation. Samples were examined daily for cytopathic effect to monitor reactivation, and the rates of reactivation and total percentage of reactivating samples were determined for KOS-NA and 7134 mutants relative to KOS. KOS began to reactivate on day 3 post-explant at 66% and reached 100% reactivation by day 5 post explant (FIG. 4). KOS-NA reactivation peaked at day 4 post explant, maintaining a reactivation efficiency of 8% throughout the study (Fisher's Exact Test, p<0.0001) (FIG.

3). 7134 reactivated on day 10 post explant, and after heat shock reached its highest levels (73%) on day 16 post explant (FIG. 4).

Whole genome sequencing of KOS-NA mutant. As our published ICP0 phosphorylation study showed, the ICP0 phosphorylation site mutant, Phos 3, was not impaired for acute replication in eyes or TG of mice, the establishment of latency, or reactivation. The differences in the pathogenesis between Phos 3 and KOS-NA strongly suggested that KOS-NA contained secondary mutations in its viral genome. To identify the secondary mutations in KOS-NA responsible for its highly attenuated phenotypes, its viral genome was sequenced in the same manner as KOS. Consequently, the genomes of KOS-NA and KOS were aligned using fast statistical alignment (FSA) to identify nucleotide polymorphisms between these two viruses. The alignment of these genomes revealed that KOS-NA contained 5 nonsynonymous mutations in three genes; UL39, which encodes ICP6, US7, which encodes the viral glycoprotein I, and RS1, which encodes the viral transcriptional regulator, ICP4.

Construction of KOS-NAR, UL39 L393P/R950H, and HrR3 R viruses. Because the acute replication, latency, and explant reactivation capabilities of KOS-NA were remarkably similar to UL39 mutant viruses in mice, it was hypothesized that the amino acid substitutions, L393P and R950H, in the open reading frame of ICP6 were responsible, at least in part, for KOS-NA's attenuated pathogenesis. To address this possibility, the UL39 gene of KOS-NA was rescued with a wild type copy, and the KOS-NA mutated UL39 gene was inserted into the genome of the HrR3 virus, an ICP6::lacZ insertion mutant of KOS. As a control, an HrR3 rescue (R) virus was generated in which the ICP6::lacZ cassette was rescued with a wild type copy of UL39. These viruses were then tested for acute replication in mice eyes and trigeminal ganglia.

Figures 5A, 5B:
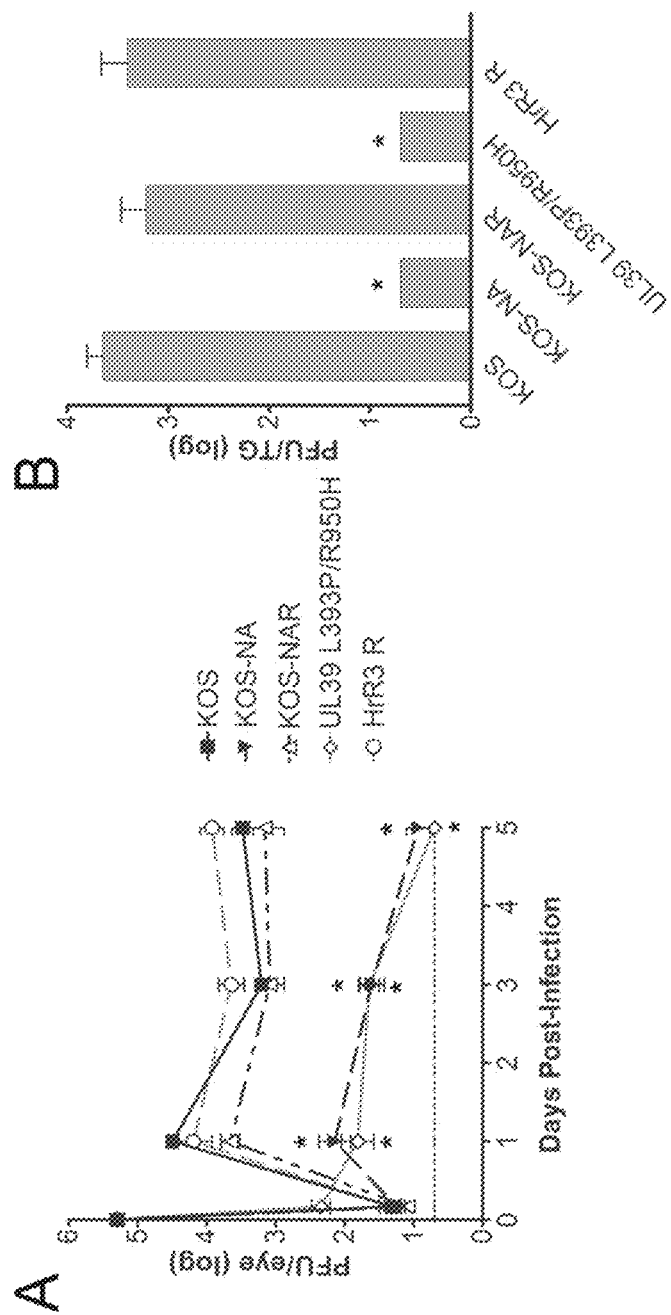
FIGS. 5A and 5B illustrates data showing that mutations in the UL39 gene are responsible for the reduced acute replication phenotype of KOS-NA. A) Acute replication of KOS-NAR, UL39 L393P/R950H, and HrR3 R in mice eyes. Mice were infected with $2 \times 10^5$ plaque forming units per eye, and tear film was collected from each eye after 4 hours and days 1, 3, and 5 post infection. The amount of infectious virus collected in each sample was determined by plaque assay. B) Acute replication of KOS-NAR, UL39 L393P/R950H, and HrR3 R in mice TG at day 5 post infection. Mice were infected as described above, and TG were collected. TG were then homogenized, and the amount of infectious virus present in each sample was determined by plaque assay. In both A and B results shown are logarithmic means, and the error bars indicate the SEM (n=8 samples per group per time point). The horizontal dotted line represents the lower limit of detection. * t test, p<0.05.

Mutations in the UL39 are responsible for the diminished acute replication phenotype of KOS-NA. To establish that the mutations identified in the UL39 gene of KOS-NA resulted in its attenuated pathogenesis, the acute replication potential of KOS-NAR and UL39 L393P/R950H in the eyes and TG of mice was tested. As shown in FIG. 5A, UL39 L393P/R950H replicated to comparable levels as KOS-NA and was reduced by 347-, 32-, and 501-fold relative to KOS at days 1, 3, and 5 post infection (t test, $p=5.5\times10^{-7}$, $p=1.2\times10^{-7}$, and $p=3.3\times10^{-9}$), respectively. When the growth of the rescue viruses, KOS-NAR and HrR3 R, was examined in this set of experiments, they replicated to similar levels as KOS (FIG. 5A).

Acute replication of the viral groups day 5 post-infection in the TG was analyzed, as this time point showed the maximum fold reduction between KOS-NA and KOS (FIG. 5B). Replication of UL39 L393P/R950H in TG at day 5 post infection could not be detected ($\geq$1412-fold reduction relative to KOS, t test $p=6.7\times10^{-15}$) (FIG. 5B). Acute replication of KOS-NAR and HrR3 R was comparable to KOS (FIG. 5B). The lack of detectable viral replication for UL39 L393P/R950H was also apparent in the TG on day 3 post infection.

Mutations in UL39 reduce ICP6 protein levels without affecting the interaction between the two subunits of the ribonucleotide reductase.

Figures 6A, 6B:
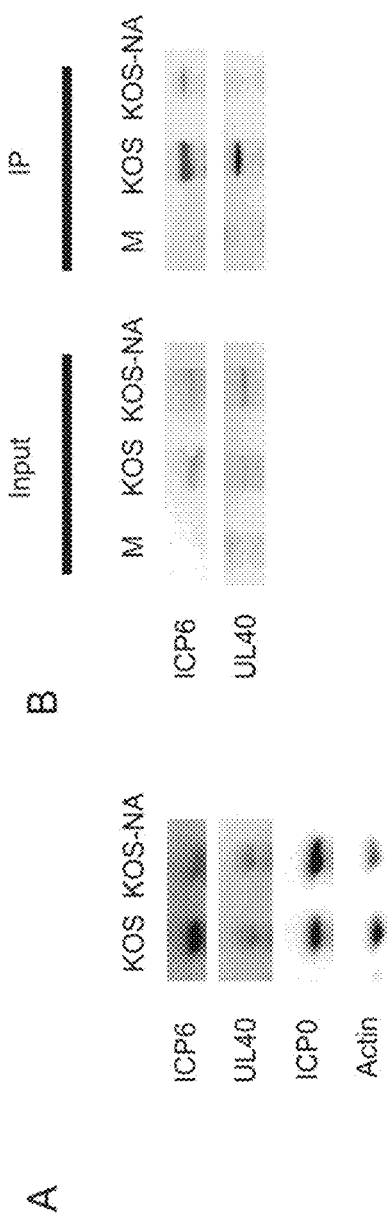
FIGS. 6A and 6B illustrate western blot analyses showing KOS-NA ICP6 protein levels and interaction with UL40. A) Vero cells were infected at MOI of 2 with KOS or KOS-NA for 24 hours. Infected monolayers were harvested, and the indicated proteins were examined by western blot analyses. ICP0 was used as a loading control for infection. B) Vero cells were mock infected or infected at an MOI of 2 for KOS and 5 for KOS-NA for 24 hours. UL40 was immunoprecipitated, and the levels of ICP6 and UL40 were analyzed by western blot.

To understand the mechanism by which mutations within the UL39 gene impact ICP6, the ICP6 protein level after KOS-NA infection versus KOS was first examined. As shown in FIG. 6A, the ICP6 protein levels after KOS-NA infection were reduced relative to those produced by KOS. On the other hand, the UL40 protein levels, produced by both viruses were comparable (FIG. 6A). This indicates that amino acid substitutions at aa 393 and/or aa 950 of ICP6 reduces its protein levels. Next it was examined whether the interaction between UL40 and ICP6 produced by KOS-NA versus KOS by immunoprecipitating UL40; in these experiments it was not possible to pull down detectable amounts of UL40 protein in KOS-NA infected cells. Cells were also infected with KOS-NA at an MOI higher than KOS, trying to express more KOS-NA ICP6 and UL40 proteins. Even under these conditions, only a very faint UL40 band and a faint band of ICP6 could be detected after immunoprecipitating UL40 (FIG. 6B), in contrast to the robust UL40 pulled down from KOS, and consequently a stronger ICP6 band (FIG. 6B). This result suggests that reduced ICP6 levels expressed by KOS-NA might influence the structure of UL40, and this is why it was difficult to pull it down with our antibody. On the other hand, the mutations in the KOS-NA UL39 gene apparently do not affect the interaction with UL40, as indicated by the faint ICP6 band pulled down when UL40 was immunoprecipitated (FIG. 6B).

Discussion

A virus, KOS-NA, has been isolated with two nonsynonymous mutations in the UL39 gene, which encodes the large subunit of ribonucleotide reductase; these mutations results in the amino acid substitutions, L393P and R950H. KOS-NA containing these mutations is significantly reduced in its acute replication in the mice eyes and TG, is greatly impaired in its ability to establish latency, and poorly reactivates from a latent infection after explant-induced reactivation.

HSV-1 ribonucleotide reductase encoded by UL39 and UL40 belongs to class I ribonucleotide reductases that have a heterodimeric structure, which is active in the α2β2 configuration and is similar to mammalian and bacterial ribonucleotide reductases. The large subunit contains the catalytic and allosteric site, which confers substrate specificity. The smaller subunit is responsible for generation of free radicals that are required for substrate activation. Viruses mutated in the UL39 gene replicate normally in dividing cells at 37° C., where the reductase activity is thought to be compensated by the cellular homolog. On the other hand, the viral reductase activity becomes important for viral DNA replication in neurons, non-dividing cells, or at elevated temperatures (e.g., 41° C.). Of relevance to this study, this enzyme complex is essential for efficient acute replication in vivo, which impacts the establishment of latency and reactivation. ICP6 is expressed early, before its small subunit partner, during viral infection in cell culture and it contains an extra N-terminal domain that is not required for HSV's ribonucleotide reductase activity. This N-terminal domain possesses anti-apoptotic, chaperone-like, and protein kinase activities. Additionally, ICP6 is a target of HSV-directed cytotoxic T lymphocytes, a function that is largely conferred by a single amino acid.

Previous studies showed that the N-terminal region of ICP6 is required for interdomain linking and that the interaction with the smaller subunit of ribonucleotide reductase is conferred by its C-terminal region. Amino acid sequence alignment studies indicate that L393 is not conserved between strain KOS and other HSV strains; syn17+ (HSV-1), McKrae (HSV-1) and HG52 (HSV-2), which, like KOS-NA, encodes a proline at this site (FIG. 7A). This could exclude L393 from being responsible for the phenotypes observed with KOS-NA. On the other hand, R950 is conserved between all HSV-1 and HSV-2 strains that were examined (i.e., KOS, syn17+, McKrae and HG52) (FIG. 7B) as well as VZV, suggesting that the R950H mutation in KOS-NA is unique. Moreover, a single aa mutation in the 961 site of HSV-1 ICP6 has been reported to reduce the ribonucleotide reductase activity of the enzyme. Although this site is important for interactions of the two ribonucleotide reductase subunits, it was previously concluded that this effect might be indirect. The 950 site is close to aa 961; aa 961 is in a region identified as "block 10" that is highly conserved between viral and cellular ribonucleotide reductases. Although the 950 site has been shown herein to be in a highly conserved region between HSV strains (FIG. 7B), this region was not as highly conserved when aligned ICP6 to the large ribonucleotide reductase subunits from HCMV (data not shown), VZV, and other eukaryotic species. Interestingly, however, R950 was still conserved between all of the herpesviruses and the eukaryotic large subunits. This highlights the functional importance of the R950 site and indicates that it is most likely the cause of KOS-NA phenotypes.

One study showed that deletion of US7, which encodes glycoprotein I (gI), can also attenuate the acute viral replication in sensory ganglia and CNS of mice without having a great effect in cell culture. Consequently, the effect of introducing the KOS-NA US7 mutation into the genome of ICP0 phosphorylation mutant, Phos 3 was tested. The results showed this mutation in the background of Phos 3 virus was able to efficiently replicate in the eyes and TG of mice, which was comparable to the wild type strain, KOS. This result indicates that the US7 mutation from KOS-NA is not responsible for its neuroattenuated phenotype.

The profound attenuation of KOS-NA in the nervous system suggests that this virus might be useful in safely stimulating immunity to HSV-1. The severe impairment KOS-NA has in establishing an efficient latent infection and reactivation from latency is likely related to its diminished acute replication phenotype in the eyes and TG of mice, as has been observed with other HSV-1 mutants. However, KOS-NA injected directly into the brain of mice also replicates to barely detectable levels. Indeed, preliminary studies indicate that KOS-NA has very good efficacy as a potential prophylactic vaccine against HSV-1.

Example 2

In Example 1 it was shown that an ICP6 mutant, KOS-NA, which carries two nonsynonymous mutations in the UL39 gene, is severely attenuated in acute replication in vivo and consequently in establishing and reactivating from latency. This mutant expressed less ICP6 protein compared to the wild type virus. Because KOS-NA preserved some expression of ICP6 protein while being severely attenuated in vivo, it was hypothesized that KOS-NA would have protective potential as the basis for a vaccine against HSV disease (e.g., HSV-1 ocular infection). Consequently, it was determined whether the replication of KOS-NA is attenuated in BALB/c mice after corneal infection, and KOS-NA was tested in an established model of vaccination followed by ocular infection of BALB/c mice to determine its potential efficacy as a vaccine. Vaccines must stimulate the strongest possible immune responses to provide optimum protective efficacy while retaining safety. Therefore vaccination of mice with the profoundly neuroattenuated KOS-NA mutant to the wild-type KOS strain of HSV-1 was compared as a gauge of KOS-NA's relative potency and effectiveness. A comparison between the protective potential of KOS-NA was also compared to a replication-attenuated mutant, which lacks the entire ICP0 open reading frame, the major transactivator of ICP6, and to a replication-incompetent ICP8 null virus.

Material and Methods

Cell lines and viruses. Viruses for immunizations were produced free of cell debris by isolation from the supernatant of infected cell monolayers using high speed centrifugation as previously described. HSV-1 strains KOS and microplaque (mP) were propagated in Vero cells. HSV-1 mutants 7134, KOS-NA and Δ41Δ29B7-2 all derive from the HSV-1 KOS strain. 7134 is an ICP0 null mutant that was propagated in L7 cells stably expressing ICP0. KOS-NA contains two non-synonymous mutations in the UL39 gene, L393P and R950H. Δ41Δ29B7-2 contains deletions in the genes encoding ICP8 and the virion host shutoff protein, and an insertion of the gene encoding murine B7-2 costimulation molecules, driven by the human cytomegalovirus immediate early promoter, into the thymidine kinase locus. Δ41Δ29B7-2 was propagated in S2 cells, a Vero cell line expressing ICP8. Virus titers were determined on L7, S2 or Vero cells as appropriate by standard plaque assay.

Mice. Female BALB/c mice were purchased from the National Cancer Institute. BALB.B mice (H-2b congenic) were purchased from The Jackson Laboratories and were bred at Saint Louis University. All mice were housed at Saint Louis University under specific pathogen-free conditions in accordance with institutional and federal guidelines and were used at 6 weeks of age under a protocol approved by Saint Louis University.

Corneal infection. BALB/c mice were deeply anesthetized and inoculated with $2\times10^5$ PFU of 7134, KOS-NA, or KOS in 5 μl vol. of normal saline onto the lightly scarified corneas. At 4 days post-infection mice were euthanized and TG were dissected. TG were disrupted individually by bead beating and virus titer in them determined by standard plaque assay. The experiment was repeated once.

Flow cytofluorometric analyses. For CD4+ T cell analyses, groups of BALB.B mice were immunized subcutaneously (s.c.) in the hind flanks with $2\times10^4$ PFU of virus suspended in 40 μl total vol. of normal saline. Cohorts of mice received an equivalent amount of supernatant concentrated from uninfected cell cultures (control supernatant) as a negative control for immunization. After 6 days, draining paraaortic and inguinal lymph nodes were removed and single cell suspensions were made. Cells were cultured for 4 hours in the presence of phorbol myristate acetate (PMA; 50 ng/ml), calcium ionophore A23187 (1 μg/ml), and GolgiStop (0.67 μl/ml; PharMingen). Cells were then treated with Fc block, followed by anti-CD3 and anti-CD4, and subsequently fixed and permeabilized using a cytostain kit (PharMingen), and stained with anti-IFNγ. Flow cytofluorometric analysis was performed using an LSRII (Becton Dickinson) and FloJo 8.0 software. The experiment was repeated twice.

Immunization of mice for vaccine efficacy studies. Hind flanks of mice were injected s.c. with $5\times10^5$ PFU (high dose), $1\times10^5$ PFU (medium dose) or $2\times10^4$ PFU (low dose) of KOS-NA, 7134, Δ41Δ29B7-2 or control supernatant suspended in 40 μl total vol.

ELISpot assays. Groups of BALB.B mice were immunized s.c. with $2\times10^4$ PFU of the various vaccine strains or an equivalent amount of control supernatant. Draining lymph nodes were removed 6 d later and single cell suspensions made. For CD8 ELISpots, $6\times10^4$ or $2\times10^4$ cells from individual mice were added per well in duplicate to Milliscreen-HA plates (Millipore) previously coated with antibody to IFNγ (BD Pharmingen). HSV-1 gB peptide 498-505 (3, 9) was added to the cultures at 0.2 µM final concentration. Control wells received medium. After incubation for 20 hr, plates were washed extensively to remove cells and captured IFNγ was detected using a biotinylated anti-IFNγ antibody (BD Pharmingen), followed by streptavidin conjugated to alkaline phosphatase (BDPharmingen) and 3-amino-9-ethylcarbazole (AEC) substrate (Sigma). Spots were counted using an Immunospot plate reader (Cellular Technology, Ltd.). The average of spots in control wells was subtracted from the number of spots in wells containing antigen. For CD4 ELISpots, cells were added at $1\times10^6$ or $3\times10^5$ cells per well. HSV-1 KOS inactivated by ultraviolet light was added at a concentration of $1\times10^5$ PFU/well prior to inactivation. For post-challenge assessments, cervical lymph nodes were removed 4 days post-challenge and prepared as described above.

Quantitation of serum antibodies. Blood was collected from the tail vein of mice 21 days after immunization. Serum was prepared by clot retraction and analyzed by ELISA as previously described. Anti-mouse-IgG-biotin (R & D Systems, Minneapolis, Minn.) was used as secondary antibody and detected using streptavidin-HRP followed by o-Phenylenediamine dihydrochloride (OPD) substrate (Sigma, St. Louis, Mo.). Plates were read at 490 nm on a BioRad 680 reader. Antibody titers were determined by comparison to standard curves generated with serum containing known concentrations of IgG captured on plates coated with goat-anti-kappa light chain antibody (Caltag) as previously described.

Challenge and post-challenge assessments. Four wk after immunization, mice were anesthetized by intraperitoneal injection of ketamine/xylazine, and infected with 5 µl HSV-1 mP inoculated onto each scarified cornea for a dose of $4\times10^5$ PFU/eye. To measure virus replication in the corneal epithelium, eyes were gently swabbed with moistened cotton-tipped swabs at 4 hours and days 1 through 5 post-infection. Swabs for each mouse were placed together in 1 ml PBS and frozen at −80° C. until assayed. Virus yield was quantified on Vero cell monolayers by standard plaque assay. After challenge, body weight, signs of disease and survival were monitored on a daily basis. Mice were weighed individually and mean change from initial body weight was calculated daily for each group. Blepharitis scores were assigned in masked fashion based on the following scale: 0, no apparent signs of disease; 1, mild swelling and erythema of the eyelid; 2, moderate swelling and crusty exudate; 3, periocular lesions and depilation; and 4, extensive lesions and depilation. Mean daily disease score was calculated for each group. Keratitis was assessed at 9 d and 14 d post-challenge using and ophthalmoscope and scored in masked fashion based on the following scale: 0, no apparent signs of disease; 1, mild opacity; 2 moderate opacity with discernible iris features; 3, dense opacity; 4, dense opacity with ulceration. Virus replication in neural tissue was analyzed by dissection of TG and brainstems from a cohort of mice 3 days or 5 days after challenge. Tissues were stored frozen until use. For virus titer determination, tissues were thawed and disrupted using a Mini-Bead Beater (BioSpec, Inc.), and then diluted for standard plaque assay.

Real time PCR to determine viral DNA loads. TG were dissected 4 weeks post-challenge from mice immunized and infected as above. DNA was isolated from individual TG using a QIAamp DNA Mini Kit (Qiagen). PCR reactions were run in 25 µL reaction volume using FastStart SYBR Green Master (Rox) (Roche), and primers at 300 nM final concentration. For GAPDH (337 bp product amplified), reactions used 10 ng template DNA. For HSV-1 UL50 (195 bp product amplified), reactions used 125 ng template DNA. Reactions were performed using an ABI Prism 7500 real-time PCR system (Applied Biosystems). Specificity was verified by melting curve analysis. The average of duplicate wells yielded the Ct value, and the UL50 signal for each sample was normalized to the GAPDH or adipsin signal content by determination of ΔCt. Fold decrease in UL50 content of TG from immunized mice relative to mice receiving control was determined using the 2(−ΔΔCt) method.

Statistical Analyses. T cell responses, concentrations of antibodies in sera, and keratitis were compared by one-way analysis of variance (ANOVA) with the Bonferroni post hoc test for multiple groups. Viral titers shed from the cornea were compared between viruses on individual days using the Student's t test. Blepharitis scores were compared on individual days using the Kruskall-Wallis test. Significance of the difference in the proportion of mice with severe keratitis was determined using the Fisher exact method. Relative levels of latent viral DNA between immunization groups were compared by ANOVA with the Bonferroni post hoc test. Comparisons of KOS-NA and KOS were performed using the Student's t test.

Results

Figures 8A, 8B:
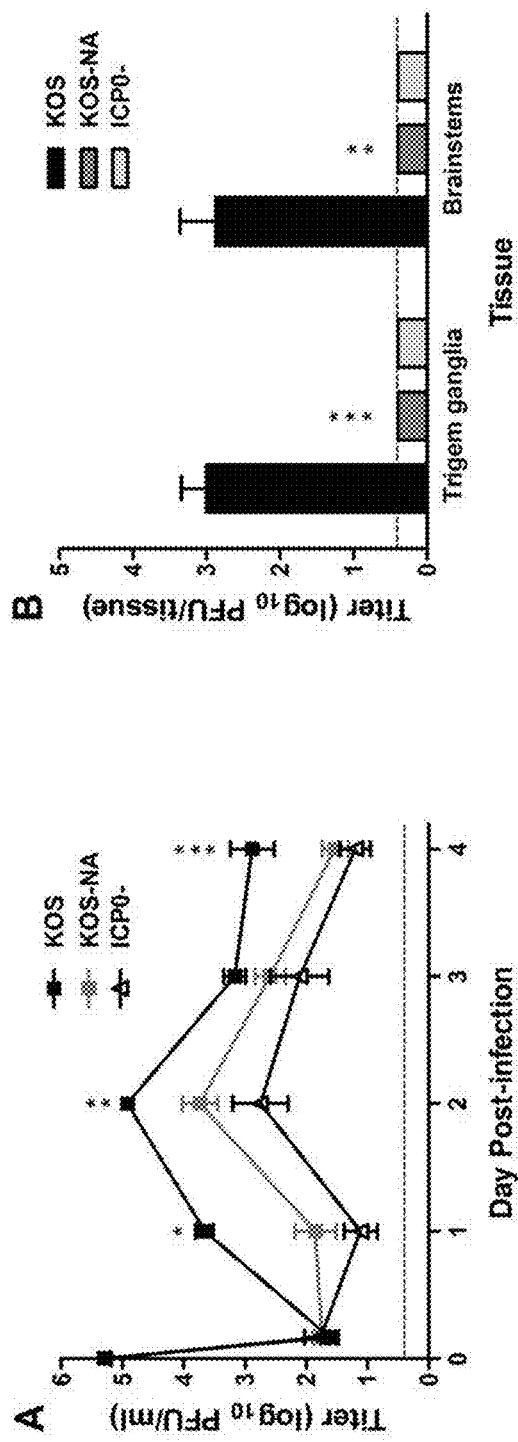
FIGS. 8A and 8B illustrate virus titers in the tear film and neural tissues after corneal inoculation. Groups of mice were inoculated on the scarified corneas with $2 \times 10^5$ PFU per eye of wild-type KOS, KOS-NA, or ICP0- (7134) virus. A) Titer of virus collected on corneal swabs was determined 4 hours and days 1-4 post-infection. T test, *, P<0.021; , P<0.0076; and *, P<0.0001 for KOS-NA compared with KOS (P>0.05 for KOS-NA compared with ICP0-virus). B) Mice were euthanized on day 5 post-infection and viral titers in TG and brainstems were determined. Values represent the mean+SEM of a total of 6 to 10 mice per group compiled from 2 independent experiments. *, P<0.01; **, P<0.001 for KOS-NA or ICP0-virus compared with KOS. Dashed lines indicate limit of detection.

Acute replication of KOS-NA in BALB/c mice. The potential value of KOS-NA as the basis for a vaccine derives from the observation that KOS-NA replication is not detectable in TG during acute replication after ocular infection of outbred CD-1 mice. In addition, KOS-NA-infected CD-1 mice do not show outward signs of HSV pathology compared to mice infected with wild-type HSV-1. As a prelude to vaccine studies in inbred mice, it was determined whether similar results would be obtained in the BALB/c strain. Replication of KOS-NA, wild-type HSV-1 (strain KOS), and an ICP0-mutant of KOS (7134) in the corneal epithelium and nervous system were compared after ocular inoculation. KOS-NA replicated with reduced efficiency in the cornea compared to KOS days 1 through 4 post-infection (FIG. 8A). In BALB/c mice, KOS-NA replicated to similar levels as the ICP0 null mutant (P>0.05), in contrast to its greater attenuation than 7134 in the CD-1 mice. Day 4 post-infection, KOS had spread to the TG and brainstem, where it replicated to high levels in both tissues (FIG. 8B). In contrast, KOS-NA and ICP0-viruses could not be detected in the nervous system. Thus, KOS-NA is as neuroattenuated as an ICP0 null virus after peripheral inoculation in BALB/c mice. This result confirms the neuroattenuation of KOS-NA observed in CD-1 mice and suggests the potential of KOS-NA as a relatively safe means to generate antiviral immunity through vaccination. KOS-NA is more immunogenic than two other viruses with vaccine potential.

Figures 9A, 9B, 9C, 9D:
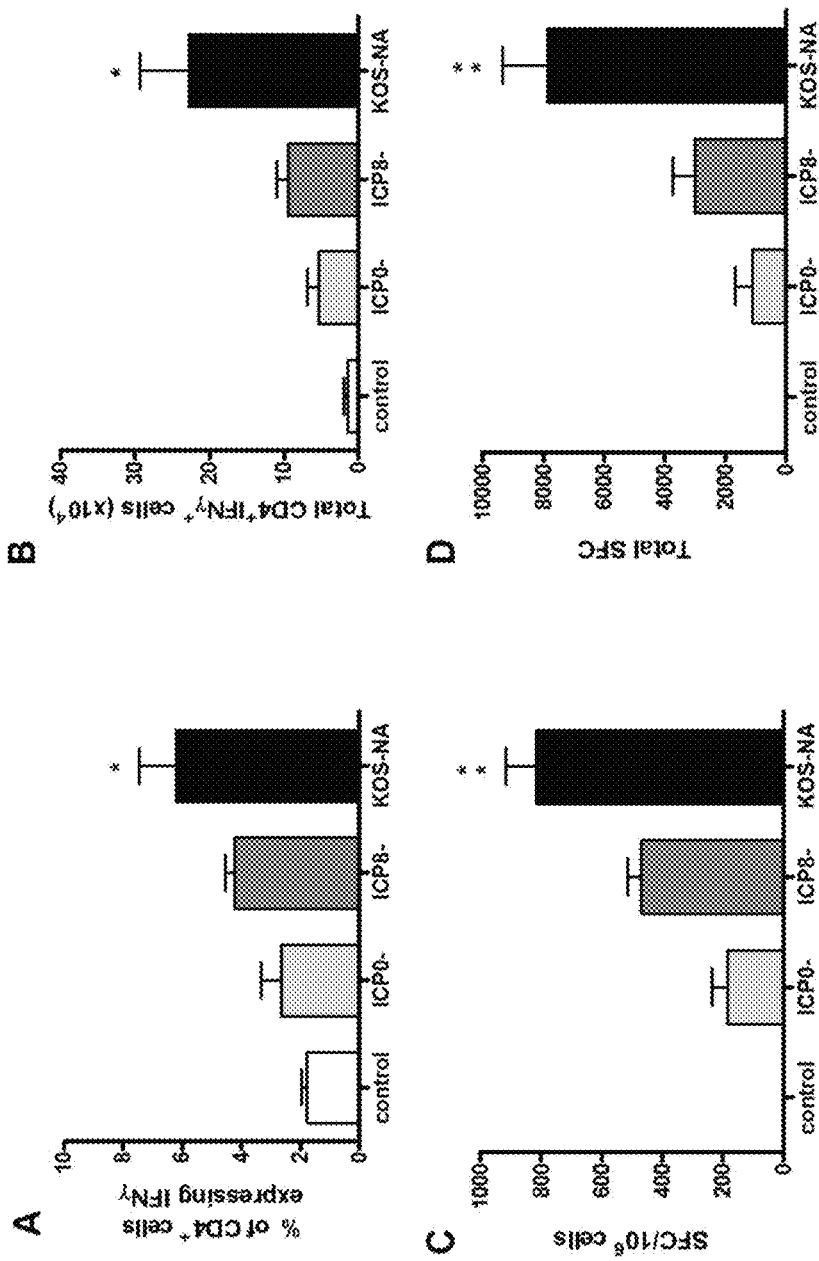
FIGS. 9A-9D illustrate T cell responses to vaccination. Mononuclear cells were isolated from the draining lymph nodes 6 days after immunization of BALB.B mice with $2 \times 10^4$ PFU of the indicated virus or control supernatant. Activated CD4 T cells in draining lymph nodes were quantified by stimulation with PMA and ionomycin followed by intracellular staining for IFNγ. A) Percentage of CD4+ T cells that are IFNγ+. B) Total number of CD4+ IFNγ-producing cells in the draining lymph nodes. Results are the mean of numbers from individual mice compiled from 3 independent experiments (total mice, 5 for control and 6 to 9 for vaccine groups). *P<0.05 for control or ICP0-virus compared with KOS-NA. HSV-specific CD8 T cell responses were compared using gB498-505 peptide as the stimulus in an IFNγ ELISpot. C) Spot-forming cells (SFC) per million lymph node cells. D) Total number of SFC in the draining lymph nodes. Results are the mean of numbers from individual mice compiled from 3 independent experiments (total mice, 7 for control and 8 to 11 for vaccine groups). **P<0.001 for control supernatant or ICP0-virus compared with KOS-NA. (P<0.05-0.01 for ICP8-virus compared with KOS-NA.)

Because KOS-NA consistently showed neuroattenuation, experiments were undertaken to determine its potential as the basis for an effective prophylactic vaccine against ocular disease caused by HSV-1. The capacity of KOS-NA to stimulate immune responses relative was compared to 7134, a replication-competent virus lacking ICP0, and to a replication-defective form of live virus vaccine (Δ41Δ29B7-2) that cannot express two viral proteins (ICP8-, vhs-) and encodes murine B7-2 costimulation molecules. Because T cell responses are critical to effective immune-mediated inhibition and clearance of HSV infection, T cell responses induced by the different forms of the vaccines 6 days after immunization were assessed. To analyze CD4+ T cell responses, cells from the draining lymph nodes were stimulated with PMA and ionomycin and stained intracellularly for IFNγ. A greater percentage (FIG. 9A) and absolute number (FIG. 9B) of CD4+ T cells produced IFNγ in mice receiving KOS-NA compared with those immunized with control supernatant, ICP0-, or ICP8-/vhs-viruses, suggesting that CD4+ T cells were activated in response to the virus vaccine. Response to an immunodominant, Kb-restricted HSV epitope (gB498-505) was used to monitor the strength of the CD8+ T cell response to vaccine in congenic BALB.B mice. Cells isolated from the draining lymph nodes were incubated with peptide representing the gB498-505 epitope, and IFNγ-producing cells were enumerated by ELISpot. More HSV-specific CD8+ T cells were found in the draining lymph nodes of KOS-NA-immunized mice than mice immunized with ICP0- or ICP8-/vhs-virus when compared on the basis of spot-forming cells per million lymph node cells (FIG. 9C) or total spot-forming cells in the draining lymph nodes (FIG. 9D). These data indicate that KOS-NA elicits a robust HSV-specific CD8+ T cell response.

Figure 10:
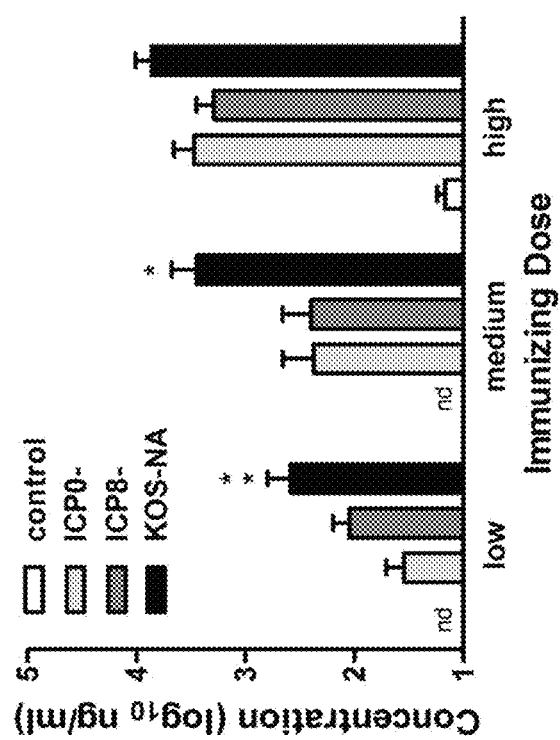
FIG. 10 illustrates titers of HSV-specific antibody in immunized mice. Groups of BALB/c mice were immunized with high ($5 \times 10^5$ PFU), medium ($1 \times 10^5$ PFU), or low ($2 \times 10^4$ PFU) doses of the indicated viruses, and 1 group of mice was immunized with control supernatant of uninfected cells. Blood was collected 21 days post-immunization, and HSV-specific serum IgG was quantified by ELISA. Data represent the geometric mean titer for 12 mice per group ±SEM, and are the combined results of 2 independent experiments with similar results. *, P<0.01; **, P<0.001 for KOS-NA compared to the ICP0-virus. (P<0.05 for KOS-NA compared to the ICP8-virus). nd, not detected.

The capacity of the vaccines to elicit HSV-specific antibody was determined by immunizing groups of mice s.c. with $5 \times 10^5$ PFU (high), $1 \times 10^5$ PFU (medium) or $2 \times 10^4$ PFU (low) doses of the viruses or control supernatant. Serum was obtained from vaccinated mice 21 days after immunization, and HSV-1-specific antibody titers were determined by ELISA. As shown in FIG. 10, KOS-NA induced a higher concentration of HSV-specific IgG than ICP0- or ICP8-/vhs-viruses, with the most pronounced differences at the low and medium doses. These results, taken together with the T cell responses, demonstrate that KOS-NA elicits a stronger antiviral immune response than an ICP0-virus or an ICP8-/vhs-virus.

Figures 11A, 11B, 11C:
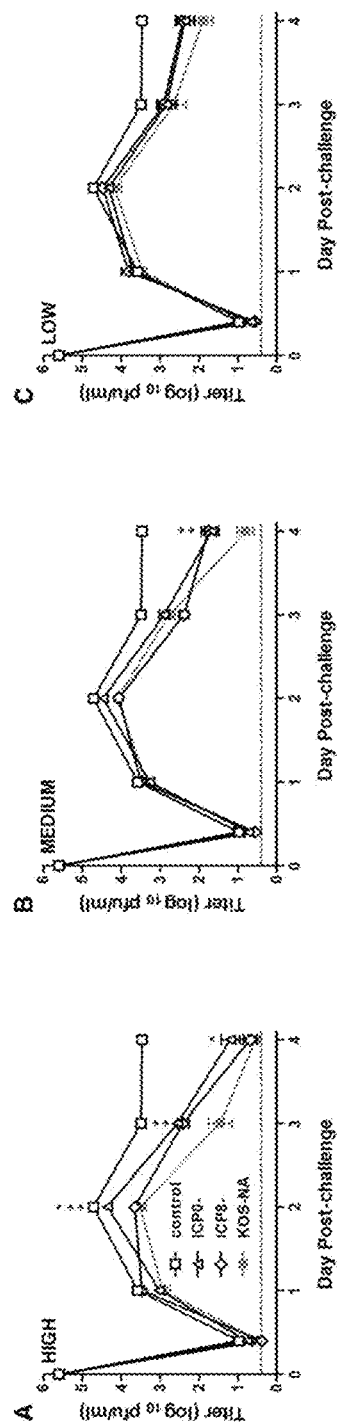
FIGS. 11A-11C illustrate eye titers of challenge virus shed from the corneal epithelium. Groups of 10 BALB/c mice vaccinated with the A) high, B) medium, or C) low dose of virus vaccine or control supernatant as described in FIG. 10 were challenged with HSV-1 strain mP ($4 \times 10^5$ PFU/eye) 4 weeks post-immunization. Eyes of 6 mice per group were swabbed at the indicated times and titer of challenge virus in them was determined. The experiment was repeated once. Eye swab data represent the geometric mean±SEM of the combined results from the two independent experiments (total mice, 12 per group). The control group is the same for all three graphs. *, P<0.00134; , P=0.002-0.0057; and *, P<0.0001 for KOS-NA compared with the ICP0-virus. Dashed lines indicate limit of detection.

KOS-NA vaccination protects mice from subsequent corneal infection with HSV-1. Next it was assessed how effectively immunization with KOS-NA could protect mice from ocular HSV-1 infection. All vaccination groups were challenged by inoculation of a virulent, heterologous HSV-1 strain onto the scarified corneas 4 wk after immunization. The corneal epithelia were swabbed over time post-challenge to determine the extent to which immunization with KOS-NA limited replication of the challenge virus. Less challenge virus replication was detected in the eyes of mice immunized with any of the vaccine viruses compared to those immunized with control supernatant, regardless of immunizing dose (FIGS. 11A-11C). Immunization with the high dose of KOS-NA significantly decreased corneal shedding of the challenge virus from 2 to 4 days post-challenge compared with the ICP0-vaccination group (FIG. 11A). KOS-NA remained more effective than both the ICP0- and ICP8-/vhs-viruses when given at the medium dose in that it almost complete controlled replication by 4 days post-challenge (FIG. 11B). At the low immunizing dose, the 3 vaccine strains showed similar capacities to reduce challenge virus replication (FIG. 11C).

Figures 12A, 12B, 12C:
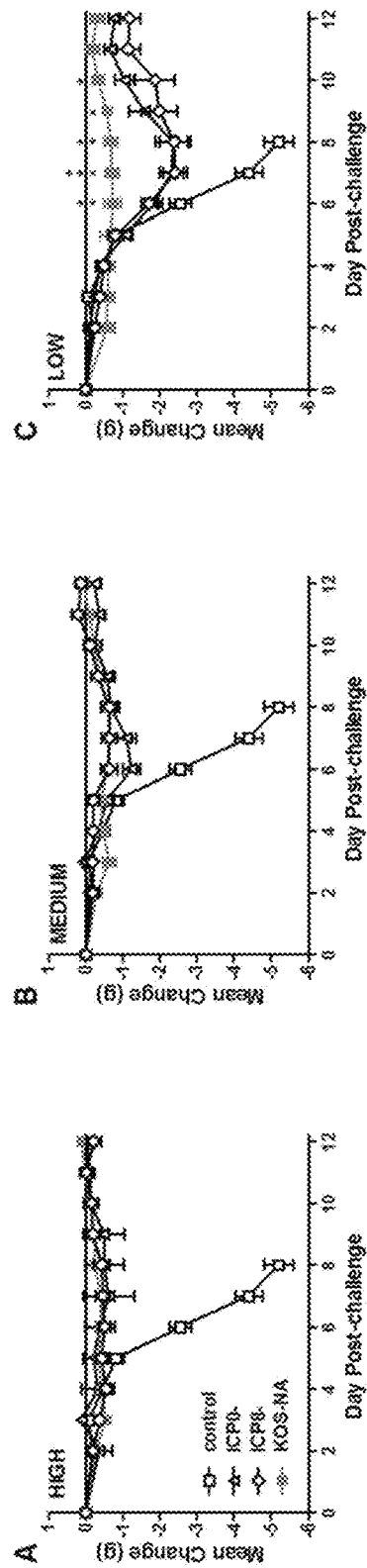
FIGS. 12A-12C illustrate body weight change upon virus challenge. The groups of 10 BALB/c mice described in FIG. 11 were weighed prior to challenge and at the indicated times post-challenge. Data are the mean change in weight ±SEM for each group and represent the combined results from two independent experiments (total mice, 20 per group). *, P=0.02; , P=0.002; and *, P<0.0001 for KOS-NA compared with the ICP0-virus.

Daily change in body weight was monitored post-challenge to assess the overall fitness of mice vaccinated with KOS-NA versus the other viruses. Mice that were immunized with control supernatant had a noticeable loss of weight by day 6 post-challenge, which further decreased until day 8 when most of the mice died (FIGS. 12A-12C). In contrast, mice immunized with the high or medium doses of any of the vaccine viruses maintained their body weight throughout the 12 day trial period. Differences among the vaccinated mice became apparent at the low immunizing dose: Mice immunized with KOS-NA maintained their weight over the course of the experiment, whereas mice immunized with the ICP0- or ICP8-/vhs-viruses showed significant loss of weight compared with KOS-NA, beginning day 6 post-challenge and extending to days 11 to 12. These results indicate that KOS-NA at the low viral dose protected mice better than ICP0- or ICP8-/vhs-viruses from weight loss.

Figures 13A, 13B, 13C:
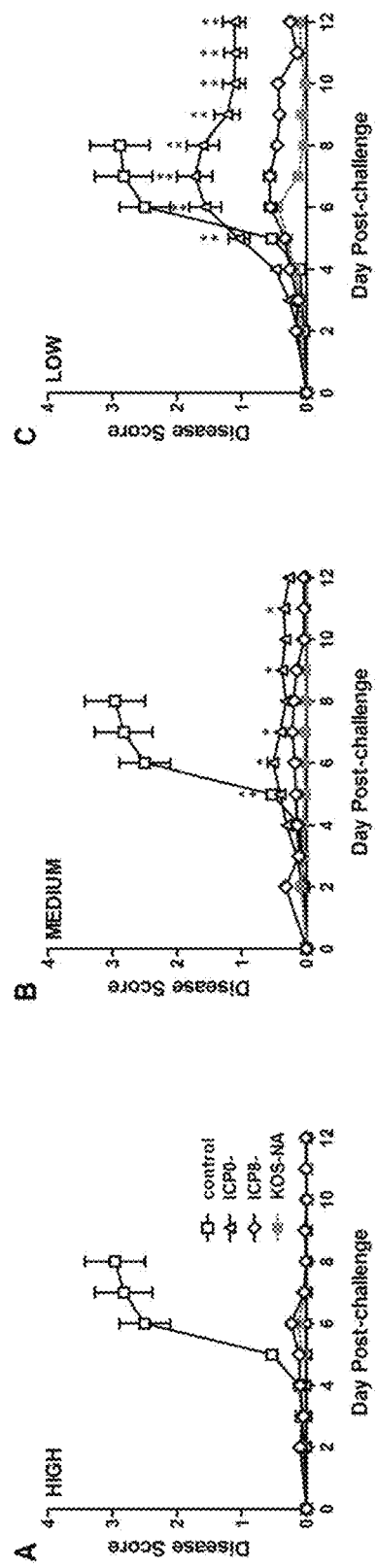
FIGS. 13A-13C illustrate protection of mice from blepharitis after corneal challenge. Groups of mice as described in FIG. 11 were scored daily for signs of eyelid disease (blepharitis). Values are the mean±SEM of 36 to 40 eyes per group and are the combined results of two independent experiments. *, P=0.01-0.043 and **, P=0.008-<0.001 for KOS-NA relative to the ICP0-virus.

Disease of the eyelid and cornea are two prominent pathologic features of HSV-1 ocular infection. Blepharitis and keratitis were therefore scored post-challenge to determine the efficacy of ocular protection. At the highest immunization dose tested, the three virus vaccines protected nearly all mice from blepharitis (FIG. 13A). At the medium dose, KOS-NA and ICP8-/vhs-prevented most mice from developing blepharitis. In contrast, protection from periocular disease was less robust with the ICP0-vaccinated group over several days post-challenge compared with the two other vaccines (FIG. 13B). This difference between the mice immunized with ICP8- and KOS-NA viruses and the ICP0-virus became most apparent at the low vaccine dose, which showed significantly more blepharitis beginning day 5 post-challenge (FIG. 13C).

Figures 14A, 14B, 14C:
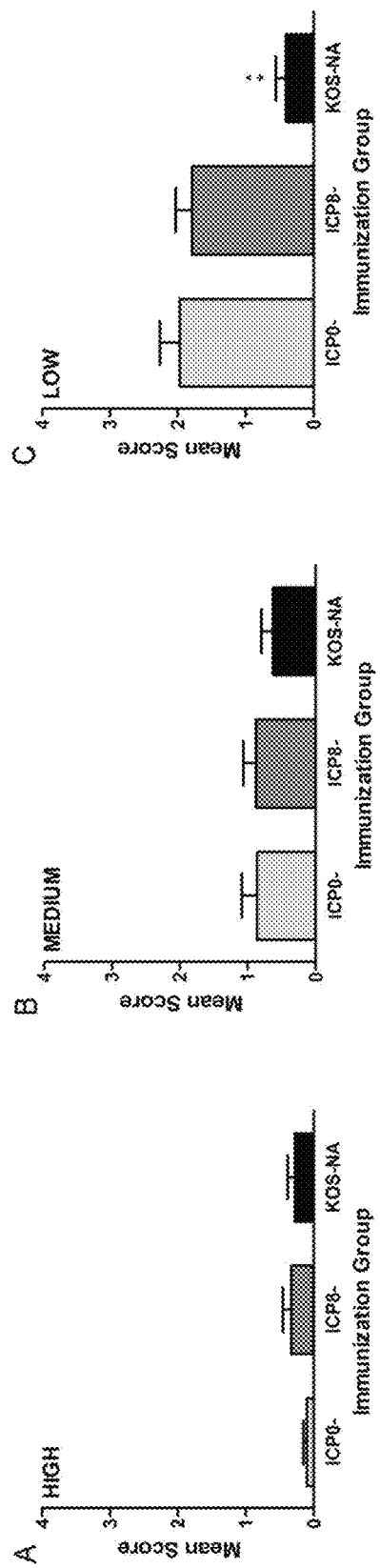
FIGS. 14A-14C illustrate protection of mice from keratitis after corneal challenge. The eyes of the same groups of mice as described in FIG. 11 were examined at 14 days post-challenge for signs of corneal disease (keratitis). Values represent the mean keratitis score+SEM of eyes from surviving mice (36 to 40 eyes per group). **, P<0.001 for KOS-NA compared with ICP8- or ICP0-virus and are the combined results of two independent experiments.

Keratitis was evaluated in all immunization groups 14 days post-challenge (FIGS. 14A-14C). All viruses protected mice from developing keratitis when given at the high or medium doses (FIGS. 14A and 14B), but only KOS-NA continued to protect the mice from developing keratitis at the low immunizing dose (FIG. 14C). Indeed, only 5% of eyes of mice previously immunized with the low dose of KOS-NA developed severe (sight impairing) keratitis, but severe keratitis developed in 45% of eyes of mice in the ICP0- and ICP8-/vhs-immunization groups (p<0.0004; data not shown). Results were similar at day 9 post-challenge (p<0.001; data not shown). Thus, a single dose of KOS-NA as low as $2 \times 10^4$ PFU almost completely protected the corneas from disease, whereas sight in half the eyes of mice immunized with the ICP0- or ICP8-/vhs-strains was badly compromised at the lowest immunizing dose.

Figures 15A, 15B, 15C, 15D, 15E, 15F:
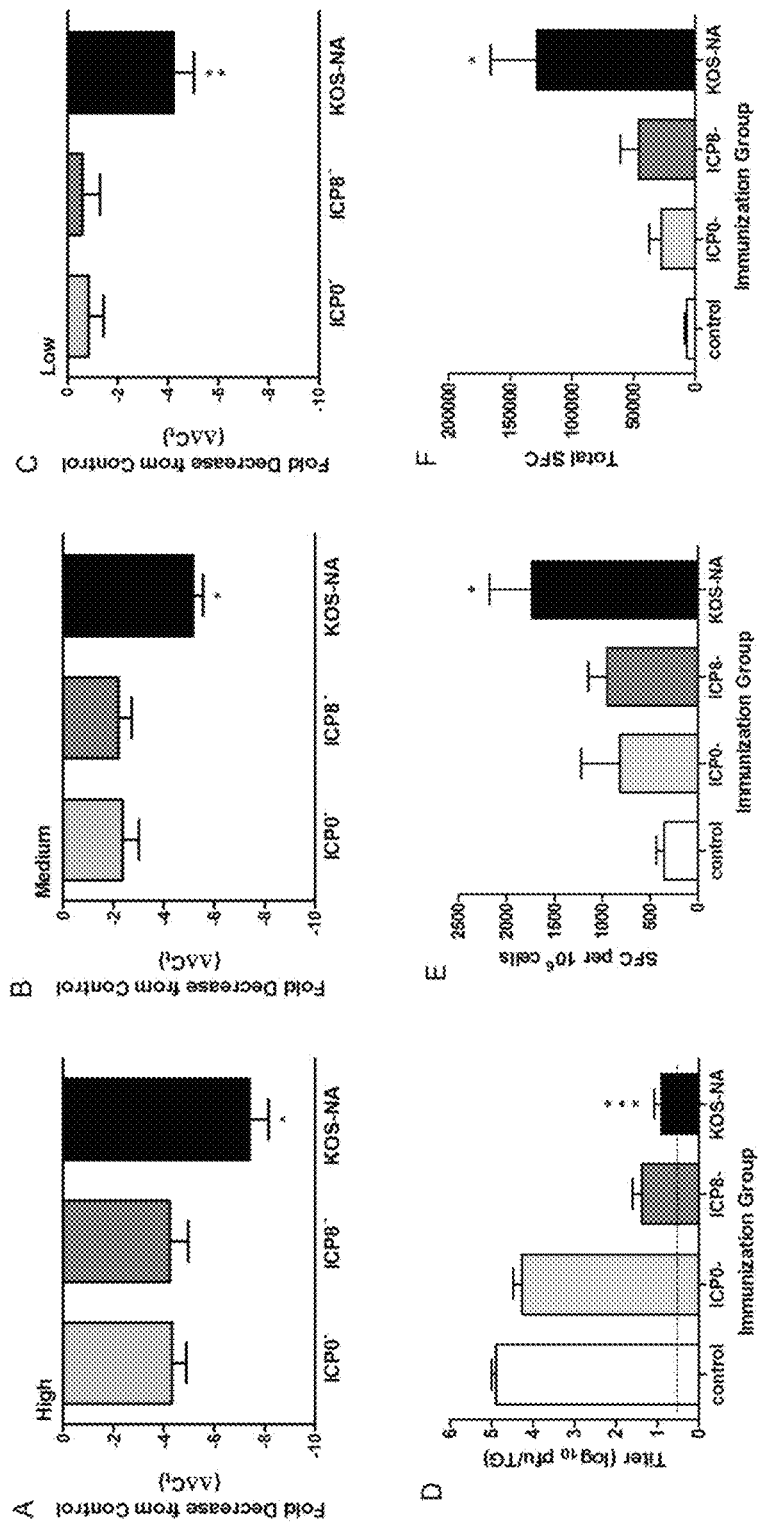
FIGS. 15A-15F illustrate data showing that immunization with KOS-NA impairs the establishment of latency of the challenge virus. Groups of mice immunized with the indicated virus or medium were infected with challenge virus as described in FIGS. 11A-11C) One month post-challenge, TG were removed and DNA was extracted. Relative viral DNA content was assessed by real-time PCR using primers for HSV-1 UL50 gene after normalization to the cellular mouse adipsin gene. Data represent the relative mean fold decrease of latent genome in 5 to 14 TG of virus-immunized mice compared with 3 TG from mice immunized with control supernatant and are the results from one of two experiments performed. HSV-1 DNA in some TG from KOS-NA high and KOS-NA medium groups were below the limit of detection. These TG were assigned a cycle number at the limit of detection for statistical purposes. *, P<0.05; , P<0.01 by ANOVA for TG from KOS-NA compared with all other groups. Additional mice were immunized with $2 \times 10^4$ PFU of the indicated viruses and challenged 1 month later as described in FIG. 11. D) TG were removed 4 days post-challenge and challenge virus titer in disrupted tissue was determined. *, P<0.001 by ANOVA for KOS-NA compared with ICP0-virus. Data are the mean+SEM of 7 to 8 mice (14 to 15 TG) compiled from 2 independent experiments. Also 4 days post-challenge, cervical lymph nodes were removed and used in an IFNγ ELISpot assay for HSV-specific CD8+ T cells with gB498-505 as stimulus. E) Spot-forming cells (SFC) per $1 \times 10^6$ cells, *P<0.05 for control compared with KOS-NA; F) total SFC per mouse; *P<0.01 for control or ICP0-virus compared with KOS-NA. (P<0.05 for ICP8-virus compared with KOS-NA). Results are the mean of individual mice compiled from 2 independent experiments (total mice, 6 per group).

Because vaccination of mice with KOS-NA impaired acute replication of challenge virus and reduced development of blepharitis and keratitis, it was undertaken to determine whether KOS-NA was effective in limiting challenge virus infection of the nervous system. The TG of latently infected mice were removed 28 days post-challenge, and relative viral genome loads for all samples were quantified by real time PCR. Prior immunization with the high or medium dose of any of the three vaccine viruses reduced the load of latent virus genome after challenge relative to the control-immunized mice (FIGS. 15A and 15B). In addition, KOS-NA protected the TG of mice from latent infection by challenge virus markedly (2- to 4-fold) better than either the ICP0- or ICP8-/vhs-viruses at every immunization dose (FIGS. 15A-15C). These data likely underestimate the differences between virus- and control-immunized animals because the majority of mice immunized with control supernatant did not survive challenge, and because HSV-1 DNA in some TG from the KOS-NA high and medium immunization groups was below the level of detection. These results indicate that immunization with KOS-NA effectively reduces latent infection of the nervous system upon challenge with HSV-1 compared with the ICP0- and ICP8-/vhs-virus vaccines.

The possible mechanisms for reduction in latent infection of the TG were investigated next. Immunized mice were challenged as before and infectious virus in the TG was assessed 4 d post-challenge. Mice previously immunized with KOS-NA had much less challenge virus in the TG acutely after challenge compared to mice immunized with ICP0-virus (FIG. 15D). Interestingly, ICP8-/vhs-virus vaccine also effectively controlled acute infection of the TG (FIG. 15D). CD8+ T cells have been linked to suppression of latent virus reactivation from the trigeminal ganglia, and may be important in preventing establishment of latency. Therefore, HSV-specific CD8+ T cell responses in response to corneal challenge were assessed. More CD8+ IFNγ-producing T cells specific for the gB498-505 epitope were observed in the cervical lymph nodes of all groups of immunized mice 4 d after challenge compared with mice immunized with control supernatant, whether evaluated on the basis of spot-forming cells per 106 lymph node cells (FIG. 15E) or total spot-forming cells (FIG. 15F).

Figures 16A, 16B, 16C, 16D, 16E:
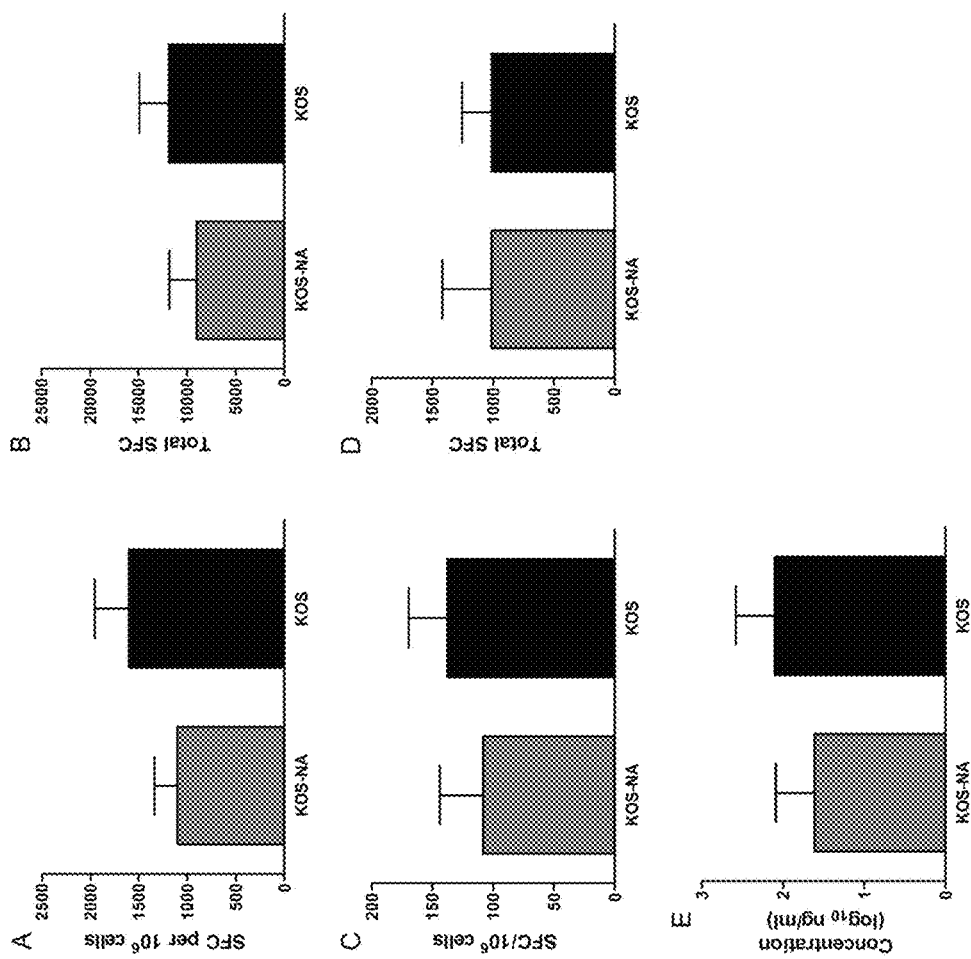
FIGS. 16A-16E illustrate data showing that neuroattenuated KOS-NA stimulates immune responses similar to wild-type strain KOS. Groups of BALB/c mice were immunized s.c. with $2 \times 10^4$ PFU (low dose) of KOS-NA or KOS, and immune responses were evaluated. Antigen-specific IFNγ-producing cells in draining lymph nodes were enumerated by ELISpot assay 6 d post-vaccination, and HSV-specific IgG in the serum 21 days post-vaccination. A) CD8+ IFNγ-producing cells specific for the gB498-505 epitope per $10^6$ lymph node cells from individual mice, and B) total CD8+ IFNγ-producing cells (10 mice per group); C) CD4+ IFNγ-producing cells per $10^6$ lymph node cells from individual mice, and D) total CD4+ IFNγ-producing cells responding to inactivated virus antigen (11 mice per group). E) Concentrations of HSV-specific serum IgG (8 mice per group).
Figures 17A, 17B:
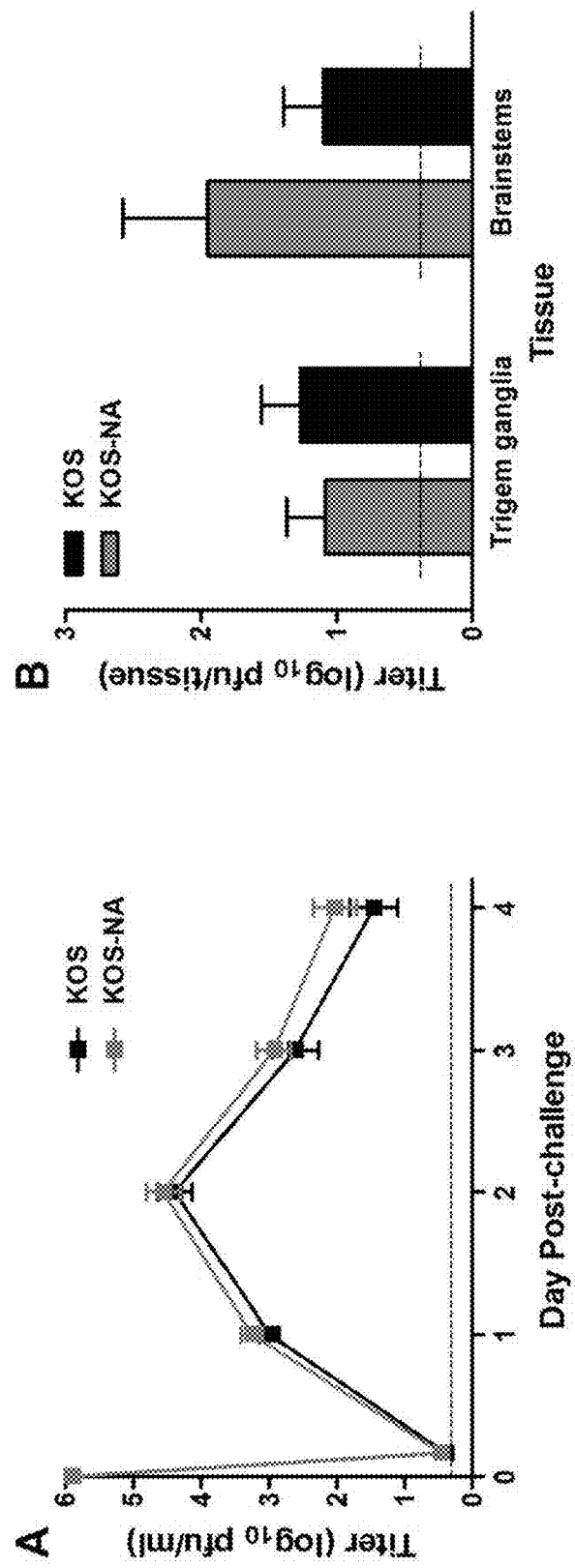
FIGS. 17A and 17B illustrates data showing that mice immunized with KOS-NA or KOS are equivalently protected from challenge. Mice immunized with $2 \times 10^4$ PFU of KOS-NA or KOS were challenged with $4 \times 10^5$ PFU of HSV-1 strain mP and protection from acute infection was assessed. A) Titer of virus shed from the corneal epithelium over time post-challenge. B) Virus titer in the TG and brainstems 4 days post-challenge. Data are the combined results of two independent experiments with 8 mice per group. Dashed lines indicate the limit of detection.

Comparative immunogenicity and efficacy of attenuated KOS-NA and wild-type KOS. The KOS-NA stimulated much stronger immune responses and protective capacity than an ICP0 null mutant, 7134, even though KOS-NA was nearly as attenuated as 7134 for replication in the cornea and did not replicate in the nervous system when directly inoculated onto the corneal surface. Therefore, the relative immunogenicity and protective capacity of attenuated KOS-NA compared with its wild-type parental strain KOS was tested. Groups of mice were immunized s.c. with $2 \times 10^4$ PFU of KOS-NA or the wild-type HSV-1 KOS strain were evaluated for T cell responses, antibody titer and capacity to resist HSV-1 challenge. The number of IFNγ-producing CD8+ T cells per 106 lymph node cells (FIG. 16A) and the total number of spot-forming cells (FIG. 16B) in the draining lymph nodes were slightly higher in mice immunized with KOS compared with KOS-NA. The number of IFNγ-producing CD4+ T cells stimulated by immunization with KOS or KOS-NA was equivalent (FIGS. 16C and 16D). HSV-specific antibody levels in the serum were not significantly different between the two groups (FIG. 16E). After challenge, no difference was seen in levels of challenge virus replication in the cornea at any time (FIG. 17A). The nervous systems of some mice from each group contained no measurable virus 4 d post-challenge, and titers in the remaining KOS-NA and KOS-immunized mice were not significantly different (FIG. 17B). Thus, KOS-NA is very nearly as immunogenic and protective as the wild-type virus from which it derives, although it is comparatively attenuated for replication in the periphery and strongly neuroattenuated.

Discussion

ICP6, the large subunit of ribonucleotide reductase, functions in a complex with the small subunit of the enzyme, encoded by UL40. This complex catalyzes the formation of deoxyribonucleotides from ribonucleotides, which are used in DNA synthesis. The requirement of viral ribonucleotide reductase enzymatic activity for viral DNA replication becomes essential during infection of quiescent cell lines and of neurons in vivo, where formation of deoxyribonucleotide pools by the host cell enzyme is restricted. In addition to its role in viral replication, ICP6 has chaperone-like activity, kinase activity, and an anti-apoptotic effect. Interestingly, ICP6 also stimulates a specific cytotoxic T cell response which is detected in infected TG. Cytotoxic T cells play a central role in protecting against lytic and latent HSV-1 infection and in controlling latency in infected neurons. Thus, ICP6 as a powerful inducer of CD8+ T cells may be a critical component of an effective HSV vaccine.

In a concurrent study shown herein above as Example 1, a viral mutant, KOS-NA, which carries two non-synonymous mutations in the UL39 gene, which encodes ICP6 was described. It was shown that KOS-NA is severely attenuated in its replication in TG with consequent reduction in establishing and reactivating from latency. KOS-NA still expresses ICP6, albeit in levels lower than those expressed by KOS. In contrast, ICP0-virus does not express ICP6 because ICP0 transactivates the UL39 promoter. This may at least in part explain the greater vaccine effectiveness of KOS-NA compared to the ICP0-mutant, 7134. It will be of interest to determine the extent to which ICP6 expression drives the stronger immune responses and protective effects observed here with KOS-NA compared with the replication-competent ICP0-virus.

In this study, it was demonstrated that KOS-NA replication was impaired for replication in the corneal epithelium of BALB/c mice, and it was not detected in the TG or brainstems (FIGS. 8A and 8B), mirroring previous results demonstrating neuroattenuation in CD-1 mice. These observations establish an important aspect of safety required of any live virus vaccine. When compared to two other vaccine groups, mice inoculated with KOS-NA produced the greatest number of HSV-1-specific CD8+ T cells and CD4+ IFNγ-producing T cells (FIGS. 9A-9D) and generated the highest anti-HSV-1 IgG titers (FIG. 10). Consequently, immunization with KOS-NA significantly decreased ocular shedding of the challenge virus 2-4 days post-infection at two different doses (FIGS. 11A-11C). It protected mice (at a low dose) from transient body weight loss after ocular infection with the challenge virus (FIGS. 12A-12C). Mice inoculated with KOS-NA were better protected from blepharitis (FIGS. 13A-13C) and severe keratitis (FIGS. 14A-14C) than ICP8-/vhs-/B7-2+ and ICP0-viruses after corneal challenge at the low vaccine dose. An important criterion in evaluating vaccine efficacy must be the capacity of a vaccine to reduce HSV infection and establishment of HSV latency in the peripheral sensory ganglia. Not surprisingly, KOS-NA was able to significantly diminish the establishment of latency of the challenge virus (FIGS. 15A-15C) compared to the supernatant control vaccinated mice. Protection was closely associated with larger numbers of CD8+ T cells in the TG after challenge (FIGS. 15E and 15F). The KOS-NA mutations did not affect the immunogenicity of HSV-1 because the mutant virus was nearly as immunostimulatory and protective as wild-type HSV-1 when used as a vaccine (FIGS. 16A-16E and 17A-17B). Taken together, it was concluded that KOS-NA offers the best protection from ocular and periocular infections as a prophylactic vaccine relative to another attenuated, replication-competent (ICP0-) virus, and a replication-defective (ICP8-/vhs-/B7+) virus engineered to optimize immune responses. The basis of this protection is linked to both higher levels of HSV-specific antibody and T cell responses.

This study is relatively unique in comparing different types of vaccine virus prototypes. It was demonstrated that a replication-defective virus further engineered to optimize immune responses can indeed generate stronger protective immunity than an attenuated but replication-competent, ICP0-strain. Significantly, the attenuated but replication-competent KOS-NA surpassed both of the other strains while still remaining unable to replicate in the nervous system of mice. These data also demonstrate the importance of testing different vaccine doses to differentiate between the vaccine strains. For example, all vaccine strains struggled to provide substantial protection against acute replication of challenge virus in the cornea, even at the highest immunizing dose, and the ability to discriminate between the strains in assessing this parameter was relatively limited. In contrast, the lowest immunizing dose of vaccine virus allowed the best discrimination between the protective effect of KOS-NA compared to the other strains in terms of weight loss, blepharitis and keratitis. Strikingly, KOS-NA at any immunizing dose provided better protection against latent infection of the TG, a critical measure of HSV vaccine efficacy.

Severe neuroattenuation and inability to establish latency suggest KOS-NA is an excellent vaccine candidate. However, the product of the UL39 gene is associated with a higher rate of spontaneous mutation not seen in UL39-virus. The fact that KOS-NA replicates as well as KOS in dividing cells in culture suggests there is not a strong selective pressure to generate secondary mutations that might alter its in vivo phenotypes. Nonetheless, it would likely be safer still to test the effect of combining KOS-NA mutations with other engineered mutations to avoid the possibility of developing adventitious mutations within KOS-NA that could reverse its neuroattenuation. Accordingly, studies are currently being undertaken to examine the effect of combining the KOS-NA mutations with ICP8 and/or vhs deletion.

Strikingly, although KOS-NA was attenuated for replication in the periphery compared with wild-type KOS, it rivaled KOS in induction of protective immune responses. These data comparing KOS-NA to KOS suggest that mutation of ICP6 at amino acids 393 and/or 950 has a positive impact on the immunogenicity of KOS-NA. The mechanism by which KOS-NA ICP6 mutations dramatically affects the in vivo behavior of the virus and enhance its protective potential without detectable replication in the sensory neurons will require further investigation.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference in their entirety.

We claim:

1. A mutant herpes simplex virus-1 (HSV-1) or herpes simplex virus-2 (HSV-2) comprising:
   an HSV-1 or HSV-2 genome having a mutated UL39 gene inserted therein, wherein the mutated UL39 gene comprises one or more mutations, the one or more mutations comprising a R950H substitution from the starting methionine in a protein product encoded by the UL39 gene.

2. The mutant HSV-1 or HSV-2 as in claim 1, wherein the one or more mutations further comprise one or more additional point mutations or in-frame deletions in the UL39 gene.

3. The mutant HSV-1 or HSV-2 as in claim 2, wherein the one or more mutations comprise a L393P substitution from the starting methionine in the protein product encoded by the UL39.

4. The mutant HSV-1 or HSV-2 as in claim 1, further comprising one or more additional mutations, the one or more additional mutations comprising in-frame deletions or mutations in at least one of the genes UL41, UL13, gamma34.5, US3, US9, US11, UL53, and combinations thereof.

5. The mutant HSV-1 or HSV-2 as in claim 4, wherein the one or more additional mutations comprise deletion of an open reading frame of one or more of UL41, UL13, gamma34.5, US3, US9, US11, UL53, or combinations thereof, or insertion of a stop codon at or near the N-terminus of one or more of UL41, UL13, gamma34.5, US3, US9, US11, UL53, or combinations thereof.

6. The mutant HSV-1 or HSV-2 as in claim 1, wherein the mutant HSV-1 or HSV-2 is immunogenic and avirulent, wherein the avirulence of the mutant HSV-1 or HSV-2 is characterized by one or more of:

being incapable of causing symptomatic infection or the consequence of symptomatic infection by a corresponding wild-type herpesvirus;

being able to replicate in non-neural tissue;

being impaired for replication in neural tissue; or being defective in establishing a latent infection.

7. The mutant HSV-1 or HSV-2 as in claim 1, wherein the one or more mutations render the mutant HSV-1 or HSV-2 impaired for replication and defective in establishing a latent infection.

8. The mutant HSV-1 or HSV-2 as in claim 1, wherein the mutant HSV-1 or HSV-2 is a mutant HSV-2.

9. The mutant HSV-2 as in claim 8, wherein the mutant HSV-2 is immunogenic and avirulent.

10. The mutant HSV-2 as in claim 8, the mutant HSV-2 further comprising one or more additional mutations, the one or more additional mutations comprising in-frame deletions or mutations in at least one gene selected from the group consisting of UL41, UL13, gamma34.5, US3, US9, US11, UL53, and combinations thereof.

11. An immunogenic composition comprising:
a pharmaceutically acceptable carrier; and
a mutant HSV-1 or HSV-2 that carries an HSV-1 or HSV-2 genome having a mutated UL39 gene inserted therein, wherein the mutated UL39 gene comprises one or more mutations, the one or more mutations comprising a R950H substitution from the starting methionine in a protein product encoded by the UL39 gene,
wherein the R950H substitution causes the mutant HSV-1 or HSV-2 to be avrirulent.

12. The immunogenic composition of claim 11, wherein inoculation with the immunogenic composition stimulates an immune response that protects against symptomatic infection or the consequences of symptomatic infection by a corresponding wild-type herpesvirus.

13. The immunogenic composition of claim 11, wherein the one or more mutations further comprise one or more additional point mutations or in-frame deletions in the UL39 gene.

14. The immunogenic composition as in claim 11, wherein the mutant HSV-1 or HSV-2 comprises a virion of the mutant HSV-1 or HSV-2.

15. The immunogenic composition as in claim 11, wherein the mutant HSV-1 or HSV-2 comprises HSV-2.

16. The immunogenic composition as in claim 15, wherein inoculation with the immunogenic composition stimulates an immune response that protects against infection or the consequences of infection by HSV-2.

17. A method for preventing a disease caused by HSV-1 or HSV-2, the method comprising:
inoculating a subject with at least a first dose of an immunogenic composition that includes a mutant HSV-1 or HSV-2 having a mutated UL39 gene inserted therein, wherein the mutated UL39 gene comprises one or more mutations, the one or more mutations comprising a R950H substitution from the starting methionine in a protein product encoded by the UL39 gene,
wherein inoculation with the immunogenic composition stimulates an immune response against the inoculated mutant HSV-1 or HSV-2 that protects against the disease caused by a wild-type virus from which the inoculated mutant HSV-1 or HSV-2 was derived.

18. The method of claim 17, wherein the one or more mutations further comprise one or more additional point mutations or in-frame deletions in the UL39 gene.

19. The method of claim 17, wherein inoculating a subject with the immunogenic composition can prevent the disease caused by a wild-type HSV-1 or HSV-2 from which the immunogenic composition was derived or treat a pre-existing disease caused by a wild-type HSV-1 or HSV-2 from which the immunogenic composition was derived.

20. The method of claim 17, wherein inoculation with the immunogenic composition stimulates an immune response that protects against infection or the consequences of infection by HSV-2.

* * * * *